US012398381B2

(12) United States Patent
Chung et al.

(10) Patent No.: US 12,398,381 B2
(45) Date of Patent: Aug. 26, 2025

(54) THERMOSTABLE VIRAL REVERSE TRANSCRIPTASE

(71) Applicant: Qiagen Beverly, LLC, Beverly, MA (US)

(72) Inventors: Suhman Chung, South Hamilton, MA (US); David Mark Schuster, Poolesville, MD (US); Thomas William Schoenfeld, Topsfield, MA (US)

(73) Assignee: Qiagen Beverly, LLC, Beverly, MA (US)

( * ) Notice: Subject to any disclaimer, the term of this patent is extended or adjusted under 35 U.S.C. 154(b) by 834 days.

(21) Appl. No.: 17/761,053

(22) PCT Filed: Sep. 18, 2020

(86) PCT No.: PCT/US2020/051465
§ 371 (c)(1),
(2) Date: Mar. 16, 2022

(87) PCT Pub. No.: WO2021/055729
PCT Pub. Date: Mar. 25, 2021

(65) Prior Publication Data
US 2022/0348891 A1 Nov. 3, 2022

Related U.S. Application Data

(60) Provisional application No. 62/902,183, filed on Sep. 18, 2019.

(30) Foreign Application Priority Data

Oct. 7, 2019 (EP) ..................................... 19201780

(51) Int. Cl.
*C12N 9/12* (2006.01)

(52) U.S. Cl.
CPC .. *C12N 9/1276* (2013.01); *C12N 2740/15022* (2013.01); *C12Y 207/07049* (2013.01)

(58) Field of Classification Search
CPC .................................................. C12N 9/1276
See application file for complete search history.

(56) References Cited

U.S. PATENT DOCUMENTS

| | | |
|---|---|---|
| 7,560,117 B2 | 7/2009 | Hughes et al. |
| 2014/0045244 A1 | 2/2014 | Park et al. |
| 2014/0286907 A1 | 9/2014 | Sarkis et al. |
| 2014/0363854 A1 | 12/2014 | Smith et al. |

FOREIGN PATENT DOCUMENTS

WO 2018189184 A1 10/2018

OTHER PUBLICATIONS

Hizi, Amnon, and Alon Herschhorn. "Retroviral reverse transcriptases (other than those of HIV-1 and murine leukemia virus): a comparison of their molecular and biochemical properties." Virus research 134.1-2 (2008): 203-220. (Year: 2008).*
Perry et al., "The surface envelope protein gene region of quine infectious anemia virus is not a important determinant of tropism in vitro", Journal of Virology, Jul. 30, 1992, pp. 4085-4097, vol. 66 No. 7, American Society for Microbiology, United States; cited in International Search Report.
International Search Report dated Jan. 29, 2021 filed in PCT/US2020/051465.
Beard, William A. et al., "Structure/Function Studies of Human Immunodeficiency Virus Type 1 Reverse Transcriptase," The Journal of Biological Chemistry, Nov. 11, 1994, pp. 28091-28907, vol. 269, No. 45, United States; cited in Specification.
Beard William A. et al., "Vertical-scanning Mutagenesis of a Critical Tryptophan in the Minor Groove Binding Track of HIV-1 Reverse Transcriptase," The Journal of Biological Chemistry, Nov. 18, 1998, pp. 30435-30442, vol. 278, No. 46, United States; cited in Specification.
Bebenek K. et al., "A minor groove binding track in reverse transcriptase," Nature Structural Biology, Mar. 1997, pp. 194-197, vol. 4 No. 3, Nature Publishing Group, United Kingdom; cited in Specification.
Bebenek, K. et al., "Reduced Frameshift Fidelity and Processivity of HIV-1 Reverse Transcriptase Mutants Containing Alanine Substitutions in Helix H of the Thumb Subdomain," The Journal of Biological Chemistry, Aug. 18, 1995, pp. 19516-19523, vol. 270 No. 33, United States; cited in Specification.
Boone, M. et al., "Capturing the 'ome': the expanding molecular toolbox for RNA and DNA library construction," Nucleic Acids Research, 2018, pp. 2701-2721, vol. 46 No. 6; United Kingdom; cited in Specification.
Burrell M., "Construction of cDNA Libraries," Methods in Molecular Biology, 1996, pp. 199-209; vol. 58, Humana Press, Inc., United States; cited in Specification.
Bustin, S. et al., "Variabililty of the Reverse Transcription Step: Practical Implications," Clinical Chemistry, 2015, pp. 202-2012, vol. 61 No. 1, American Association for Clinical Chemistry, United States; cited in Specification.

(Continued)

*Primary Examiner* — Robert J Yamasaki
(74) *Attorney, Agent, or Firm* — Rankin, Hill & Clark LLP

(57) ABSTRACT

The present invention provides novel engineered reverse transcriptase enzymes that afford beneficial improvements in thermal stability, processivity, cDNA yields and elimination of secondary enzymatic activity. The present invention also provides methods for amplifying template nucleic acids using such reverse transcriptase enzymes. This invention addresses deficiencies in the current state of the art reverse transcriptase enzymes in RNA detection and analysis including deficiencies in detection sensitivity, specificity, side enzyme activities, enzyme stability and synthesis capacity, especially when using template nucleic acids ranging in length, secondary structure and nucleotide content.

24 Claims, 7 Drawing Sheets
Specification includes a Sequence Listing.

(56) References Cited

OTHER PUBLICATIONS

Gerard Gary F. et al., "Purification and Characterization of the DNA Polymerase and RNase H Activities in Moloney Murine Sarcoma-Leukemia Virus," Journal if Virology, Apr. 1975, pp. 785-797, vol. 15 No. 4, American Society of Microbiology, United States; cited in Specification.

Gerard Gary F. et al., "The role of template-primer in protection of reverse transcriptase from thermal inactivation," Nucleic Acids Research, 2002, pp. 3118-3129, vol. 30 No. 14, Oxford University Press, United Kingdom; cited in Specification.

Gibson Ursula E.M. et al., "A Novel Method for Real Time Quantitative RT-PCR," Genome Research, 1996, pp. 995-1001, vol. 6 No. 10, Cold Springs Harbor Laboratory Press, United States; cited in Specification.

Hrdlickova Radmila et al., "RNA-Seq methods for transcriptome analysis," Wiley Interdisciplinary Reviews RNA, May 2016, Wiley Periodicals, Inc., United States; cited in Specification.

Huang H. et al., "Structure of a Covalently Trapped Catalytic Complex of HIV-1 Reverse Transcriptase: Implications for Drug Resistance," Science, Nov. 27, 1998, pp. 1669-1675, vol. 282, Advancement of Science, United States; cited in Specification.

Kacian D.L. et al., "Purification of the DNA Polymerase of Avian Myeloblastosis Virus," Biochimica et Biophysica Acta, 1971, pp. 365-383, vol. 246 No. 3, Elservier, The Netherlands; cited in Specification.

Lee MS et al., "Detection of Minimal Residual bcr/abl transcripts by a modified polymerase chain reaction," Blood, 1988, pp. 893-897, vol. 72 No. 3, American Society of Hematology, United States; Cited in Specification.

Matamoros, Tania et al., "Major Groove Binding Track Residues of the Connection Subdomain of human Immunodeficiency Virus Type 1 Reverse Transcriptase Enhance cDNA Synthesis at High Temperatures," Biochemistry, 2013, pp. 9318-9328, vol. 52, American Chemical Society, United States; cited in Specification.

Mizuno, Masaki et al., "Insight into the Mechanism of teh Stabilization of Moloney Murine Leukaemia Virus Reverse Transcriptase by Eliminating RNase H Activity," Biosci. Biotechnol. Biochem., 2010, pp. 440-442, vol. 74 No. 2, Japan Society for Bioscience, Biotechnology, and Agrochemistry, Japan; cited in Specification.

Moser, Michael J. et al., "Thermostable DNA Polymerase from a Viral Metagenome Is a Potent RT-PCR Enzyme," PLoS ONE, Jun. 2012, pp. e38371, vol. 7 issue 6, Public Library of Science, United States; cited in Specification.

Okello, John B. A. et al., "Quantitative Assessment of teh Sensitivity of Various Commercial Reverse Transcriptases Based on Amored HIV RNA," PLoS ONE, Nov. 2010, pp. e13931, vol. 5 issue 11, Public Library of Science, United States; cited in Specification.

Paria B.C. et al., "Expression of the epidermal growth factor receptor gene is regulated in mouse blastocysts during delayed implantation," Proc. Natl. Acad. Sci., Jan. 1993, pp. 55-59, vol. 90, Developmental Biology, United States; cited in Specification.

Sanders, Rebecca et al., "Improving the standardization of mRNA measurement by RT-qPCR," Biomolecular Detection and Quantification, 2018, pp. 13-17, vol. 15, Elservier, The Netherlands; cited in Specification.

Spiegelman, S. et al., Synthesis of DNA Complements of Natural RNAs: A General Approach, Nov. 1971, pp. 2843-2845, vol. 68 No. 11, Pro. Nat. Aca. Sci., United States; cited in Specification.

Svarovskaia, Evguenia S. et al., "Structural Determinants of Murine Leukemia Virus Reverse Transcriptase That Affects the Frequency of Template Switching," Journal of Virology, Aug. 2000, pp. 7171-7178, vol. 74 No. 15, American Society for Microbiology, United States; cited in Specification.

Telesnitsky, A et al., "Reverse Transcriptase and teh Generation of Retroviral DNA," Retroviruses, 1997, Cold Harbor Laboratory Press, United States; cited in Specification.

Warren, Luigi et al., "Transcription factor profiling in individual hematopoietic progenitors by digital RT-PCR," Proceedings of the National Academy of Sciences, Nov. 21, 2006, pp. 17807-178012, vol. 143 No. 47, National Academy of Sciences, United States; cited in Specification.

\* cited by examiner

Fig. 1

THERMOSTABLE VIRAL REVERSE TRANSCRIPTASE

This application includes a Substitute Computer Readable Form (CFR) copy of a sequence listing, which is hereby incorporated by reference. The Substitute Computer Readable Form (CFR) copy of the sequence listing was submitted on Jul. 20, 2022 via EFS-web as an ASCII text file named "QIA-52303-Substitute-Sequence-Listing.txt". The ASCII text file was created on Jul. 20, 2022, and is 72 KB in size.

FIELD OF THE INVENTION

The present invention provides novel engineered reverse transcriptase enzymes for improved detection and analysis of RNA. The present invention also provides methods for amplifying template nucleic acids using such reverse transcriptase enzymes and methods of producing said enzymes. This invention addresses deficiencies of current state of the art reverse transcriptase enzymes in RNA detection and analysis including deficiencies in detection sensitivity, specificity, side enzyme activities, enzyme stability and synthesis capacity, especially when using template nucleic acids ranging in length, secondary structure and nucleotide content.

TECHNOLOGICAL BACKGROUND

Detection and analysis of RNA can provide insight into important biological phenomena like gene expression, gene silencing, the presence and absence of important pathogens, particularly RNA viruses, and other medically important states. The ability to monitor presence or absence or changes in the amounts of messenger RNA, noncoding RNA and viral RNA allows diagnosis of important disease states like cancer or viral infections and generally facilitates research into biological processes. For these reasons, improvements in the state of the art in these analyses are highly sought.

The most common methods of RNA analysis depend on reverse transcriptase enzymes to catalyze the synthesis of complementary DNA (cDNA) using an RNA template (Spiegelman 1971, Telesnitsky 1997), which is a critical step in several related analytic and preparative methods. For example, reverse transcription PCR (RT-PCR) (Lee 1989) and its variants quantitative RT-PCR (RT qPCR), realtime quantitative RT-PCR (RT RT-PCR) (Owarzek 1992, Paria 1993, Gibson 1996) and digital RT-PCR (RT dPCR) (Warren 2006, Sanders 2018) are fundamentally two-step processes in which cDNA is synthesized by reverse transcription and amplified by PCR. Typically, these two functions are provided by separate enzymes, a reverse transcriptase (RT), often a Moloney murine leukemia virus (MMLV) RT derivative and a thermostable DNA polymerase (Pol), typically Taq Pol. The performance of these methods depends on both activities, but improvements are most commonly sought by focusing on the RT enzyme since the PCR step is generally better established and more robust.

In addition to RT-PCR, areas of RNA-centered genomics focused on transcripts, noncoding RNA, and viral genomics and metagenomics rely on variants of analytic approaches referred to collectively as RNA-Seq (reviewed in Hrdlickova 2017, Boone et al 2018). Different RNA-Seq strategies are used to address different biological questions associated with phenomena like variations in gene expression and the relative abundance of transcripts, diversity of viral genomic sequences and their evolution, intron processing and splicing and other related phenomena. In all cases, the enzyme component is critical to the generation of libraries used for sequence analysis and has a substantial impact on the overall quality and reliability of the analysis. Besides RT-PCR and RNA-Seq, cDNA synthesis has a more traditional use as a preparative method related to cloning cDNA for more focused analysis on transcripts and translated proteins (Spiegelman 1971, Burrell 1996). Optimal performance in each of these analyses places unique demands on the enzymes and the choice of RT has a strong impact on the effectiveness and reliability of the method (Okello 2010, Bustin 2015).

Engineering has refined the performance of RT in specific applications. Many RTs have inherent RNase H activities that digest the RNA component of RNA/DNA hybrids (Gerard 1975). This is a positive attribute for certain applications, but interferes with other common uses (Garces 1991). There is a secondary effect of disabling RNase H activity: besides eliminating its canonical function as a nuclease, eliminating RNase H activity by mutagenesis also improves thermostability. This allows synthesis at higher temperatures, thereby facilitating analysis of highly structured RNA targets. Additional research on MMLV RT indicates that certain domains, particularly the minor groove binding track (MGBT) and connection domain (CD), play roles in interacting with template (Beard 1994). Modifying either RNase H activity, the MGBT or CD or some combination can increase template switching (Garces 1991, Svarovskaia 2000) and affinity for template and, by extension, length of product. These improvements are beneficial to varying degrees in RT-PCR, preparation of RNA-Seq libraries and cDNA cloning.

Numerous native and engineered RTs have been examined to address the specialized needs of these different applications. Most common are derivatives of Moloney murine leukemia virus (MMLV) RT (Gerard 1975) or, less commonly, avain myeloblastosis (AMV) RT (Kacian 1971). Other RT enzymes have been derived from alternative retroviral enzymes (e.g., U.S. Pat. No. 7,560,117), phages (Moser 2012) and bacteria (Grabco 1996) but none fully addresses the needs for highly sensitive, highly specific, robust cDNA synthesis of targets ranging in length, secondary structure and nucleotide content. These limitations in the state of the art thus create a continuing need for improvements.

REFERENCES

Beard, W A., Stahl, S J., Kim, H R., Bebenek, K., Kumar, A., Strub, M P., Becerra, S P., Kunkel, T A., Wilson, S H. StructureIFunction Studies of Human Immunodeficiency Virus Type 1 Reverse Transcriptase. J. Biol. Chem. 1994, 269, 28091-7.

Beard W A, Bebenek K, Darden T A, Li L, Prasad R, Kunkel T A, Wilson S H. Vertical-scanning mutagenesis of a critical tryptophan in the minor groove binding track of HIV-1 reverse transcriptase. Molecular nature of polymerase-nucleic acid interactions. J Biol Chem. 1998 273 (46):30435-42.

Bebenek K, Beard W A, Darden T A, Li L, Prasad R, Luton B A, Gorenstein D G, Wilson S H, Kunkel T A. A minor groove binding track in reverse transcriptase. Nat Struct Biol. 1997 March; 4(3):194-7.

Bebenek, K., Beard, W A., Casas-Finet, J R., Kim, H R., Darden, T A., Wilson, S H., Kunkel, T A. Reduced Frameshift Fidelity and Processivity of HIV-1 Reverse Transcriptase Mutants Containing Alanine Substitutions in Helix H of the Thumb Subdomain. J. Biol. Chem. 1995, 270, 19516-23.

Boone M, De Koker A, Callewaert N. Capturing the 'ome': the expanding molecular toolbox for RNA and DNA library construction. Nucleic Acids Res. 2018 46(6):2701-2721.

Burrell M M. Construction of cDNA libraries. Methods Mol Biol. 1996; 58:199-209.

Bustin S, Dhillon H S, Kirvell S, Greenwood C, Parker M, Shipley G L, Nolan T. Variability of the reverse transcription step: practical implications. Clin Chem. 2015 January; 61(1):202-12.

Gerard G F, Grandgenett D P. Purification and characterization of the DNA polymerase and RNase H activities in Moloney murine sarcoma-leukemia virus. J Virol. 1975 15(4):785-97.

Gerard G F, Potter R J, Smith M D, Rosenthal K, Dhariwal G, Lee J, Chatterjee D K. The role of template-primer in protection of reverse transcriptase from thermal inactivation. Nucleic Acids Res. 2002 30(14):3118-29.

Gibson U E, Heid C A, Williams P M. A novel method for real time quantitative RT-PCR. Genome Res. 1996 6(10): 995-1001.

Hrdlickova R, Toloue M, Tian B. RNA-Seq methods for transcriptome analysis. Wiley Interdiscip Rev RNA. 2017 8(1).

Huang H, Chopra R, Verdine G L, Harrison S C. Structure of a covalently trapped catalytic complex of HIV-1 reverse transcriptase: implications for drug resistance. Science. 1998 282(5394):1669-75.

Kacian D L, Watson K F, Burny A, Spiegelman S. Purification of the DNA polymerase of avian myeloblastosis virus. Biochim Biophys Acta. 1971 246(3):365-83.

Lee M S, Chang K S, Freireich E J, Kantarjian H M, Talpaz M, Trujillo J M, Stass S A. Detection of minimal residual bcr/abl transcripts by a modified polymerase chain reaction. Blood. 1988 72(3):893-7.

Matamoros T, Barrioluengo V, Abia D, Menendez-Arias L. Major groove binding track residues of the connection subdomain of human immunodeficiency virus type 1 reverse transcriptase enhance cDNA synthesis at high temperatures. Biochemistry. 2013 52(51):9318-28.

Mizuno M, Yasukawa K, Inouye K. Insight into the mechanism of the stabilization of moloney murine leukaemia virus reverse transcriptase by eliminating RNase H activity. Biosci Biotechnol Biochem. 2010 74(2):440-2.

Moser M J, DiFrancesco R A, Gowda K, Klingele A J, Sugar D R, Stocki S, Mead D A, Schoenfeld T W. Thermostable DNA polymerase from a viral metagenome is a potent R T-PCR enzyme. PLoS One. 2012 7(6):e38371.

Okello J B, Rodriguez L, Poinar D, Bos K, Okwi A L, Bimenya G S, Sewankambo N K, Henry K R, Kuch M, Poinar H N. Quantitative assessment of the sensitivity of various commercial reverse transcriptases based on armored HIV RNA. PLoS One. 2010 5(11):e13931.

Paria B C, Das S K, Andrews G K, Dey S K. Expression of the epidermal growth factor receptor gene is regulated in mouse blastocysts during delayed implantation. Proc Natl Acad Sci USA. 1993 90(1):55-9.

Sanders R, Bustin S, Huggett J, Mason D. Improving the standardization of mRNA measurement by R T-qPCR. Biomol Detect Quantif. 2018 15:13-17.

Spiegelman S, Watson K F, Kacian D L. Synthesis of DNA complements of natural RNAs: a general approach. Proc Natl Acad Sci USA. 1971 68(11):2843-5.

Svarovskaia E S, Delviks K A, Hwang C K, Pathak V K. Structural determinants of murine leukemia virus reverse transcriptase that affect the frequency of template switching. J Virol. 2000 74(15):7171-8.

Telesnitsky A, Goff S P. Reverse Transcriptase and the Generation of Retroviral DNA. In: Coffin J M, Hughes S H, Varmus H E, editors. Retroviruses. Cold Spring Harbor (NY): Cold Spring Harbor Laboratory Press; 1997.

Warren L, Bryder D, Weissman I L, Quake S R. Transcription factor profiling in individual hematopoietic progenitors by digital RT-PCR. Proc Natl Acad Sci USA. 2006 103(47): 17807-12.

SUMMARY OF THE INVENTION

This invention provides novel engineered reverse transcriptase enzymes that afford beneficial improvements in thermal stability, length of cDNAs synthesized using an RNA template, and elimination of secondary enzymatic activity. These improvements were incorporated into the parental equine infectious anemia virus reverse transcriptase (EIAV RT) molecule by directed mutagenesis of amino acid residues residing in thumb, connection, and RNase H domains. These mutations collectively eliminate RNase H activity and increase RT activity at elevated temperature and were identified from both rational design and random mutagenesis/screening. Combining these mutations allows significant improvement in performance including the capability to synthesize cDNAs of greater than 12 kb in length at the temperatures up to 65° C.

In a first aspect, the present invention relates to a reverse transcriptase (RT) comprising two subunits, wherein the two subunits are each encoded by a variant of the polynucleotide sequence of SEQ ID NO:1, wherein the amino acid sequence encoded by the variant is at least 90% identical to the amino acid sequence of SEQ ID NO:2 or a fragment thereof, and wherein the variant comprises one or more mutations in the polynucleotide sequence of SEQ ID NO:1 causing one or more amino acid exchanges relative to the amino acid sequence SEQ ID NO:2 in the minor groove binding track (MGBT) of the RT's thumb domain and/or the RT's connection domain (CD).

The one or more amino acid exchanges according to this aspect of the invention can be caused within the encoded amino acid sequence at the amino acid positions that correspond to positions 263, 265, 267, 269, and 271 of SEQ ID NO:2, wherein the amino acid exchanges are M263V, N265K, T267N, M269A, and S271Q.

Additionally or alternatively, the one or more amino acid exchanges can be caused within the encoded amino acid sequence at the amino acid positions that correspond to positions 356, 360, 362, and 363 of SEQ ID NO:2, wherein the amino acid exchanges are I356G or I356D or I356N, N360A, G362T or G362N, and W363K or W363N or W363I, preferably I356G, N360A, G362T and W363K.

According to one embodiment, the variant of SEQ ID NO:1 further comprises one or more mutations in the polynucleotide sequence of SEQ ID NO:1 causing one or more amino acid exchanges relative to SEQ ID NO:2 in the RT's RNase H domain. The one or more amino acid exchanges according to this aspect of the invention can be caused within the encoded amino acid sequence at the amino acid positions that correspond to positions 443, 470, 476, 491, 526 and 553 of SEQ ID NO:2, wherein the amino acid exchanges are D443G, V470F, E476Q, Q491R, R526H and K553R. In a preferred embodiment, the amino acid exchanges are D443G and/or E476Q. In a highly preferred embodiment, the amino acid exchange is D443G.

According to another embodiment, the one or more mutations in the polynucleotide sequence of SEQ ID NO:1 cause one or more amino acid exchanges within the encoded amino acid sequence at the amino acid positions that correspond to positions 263, 265, 267, 269, 271 and 443 of SEQ ID NO:2, wherein the amino acid exchanges are M263V, N265K, T267N, M269A, S271Q and D443G. In a preferred embodiment, mutations in the polynucleotide sequence of SEQ ID NO:1 cause amino acid exchanges within the encoded amino acid sequence at all the amino acid positions that correspond to positions 263, 265, 267, 269, 271 and 443 of SEQ ID NO:2, wherein the amino acid exchanges are M263V, N265K, T267N, M269A, S271Q and D443G.

According to a further embodiment, the one or more mutations in the polynucleotide sequence of SEQ ID NO:1 cause one or more amino acid exchanges within the encoded amino acid sequence at the amino acid positions that correspond to positions 263, 265, 267, 269, 271, 356, 360, 362, 363 and 443 of SEQ ID NO:2, wherein the amino acid exchanges are M263V, N265K, T267N, M269A, S271Q, I356G, N360A, G362T, W363K and D443G. In a preferred embodiment, mutations in the polynucleotide sequence of SEQ ID NO:1 cause amino acid exchanges within the encoded amino acid sequence at all the amino acid positions that correspond to positions 263, 265, 267, 269, 271, 356, 360, 362, 363 and 443 of SEQ ID NO:2, wherein the amino acid exchanges are M263V, N265K, T267N, M269A, S271Q, I356G, N360A, G362T, W363K and D443G. Alternatively, mutations in the polynucleotide sequence of SEQ ID NO:1 cause amino acid exchanges within the encoded amino acid sequence at all the amino acid positions that correspond to positions 263, 265, 267, 269, 271, 356, 360, 362, 363 and 443 of SEQ ID NO:2, wherein the amino acid exchanges are M263V, N265K, T267N, M269A, S271Q, I356G, N360A, G362T, W363N and D443G. Yet alternatively, mutations in the polynucleotide sequence of SEQ ID NO:1 cause amino acid exchanges within the encoded amino acid sequence at all the amino acid positions that correspond to positions 263, 265, 267, 269, 271, 356, 360, 362, 363 and 443 of SEQ ID NO:2, wherein the amino acid exchanges are M263V, N265K, T267N, M269A, S271Q, I356D, N360A, G362T, W363K and D443G. Yet alternatively, mutations in the polynucleotide sequence of SEQ ID NO:1 cause amino acid exchanges within the encoded amino acid sequence at all the amino acid positions that correspond to positions 263, 265, 267, 269, 271, 356, 360, 362, 363 and 443 of SEQ ID NO:2, wherein the amino acid exchanges are M263V, N265K, T267N, M269A, S271Q, I356N, N360A, G362N, W363I and D443G.

According to a further embodiment, the one or more mutations in the polynucleotide sequence of SEQ ID NO:1 cause one or more amino acid exchanges within the encoded amino acid sequence at the amino acid positions that correspond to positions 263, 265, 267, 269, 271, 491, 526 and 443 of SEQ ID NO:2, wherein the amino acid exchanges are M263V, N265K, T267N, M269A, S271Q, Q491R, R526H and D443G. In a preferred embodiment, mutations in the polynucleotide sequence of SEQ ID NO:1 cause amino acid exchanges within the encoded amino acid sequence at all the amino acid positions that correspond to positions 263, 265, 267, 269, 271, 491, 526 and 443 of SEQ ID NO:2, wherein the amino acid exchanges are M263V, N265K, T267N, M269A, S271Q, Q491R, R526H and D443G. Alternatively, mutations in the polynucleotide sequence of SEQ ID NO:1 cause amino acid exchanges within the encoded amino acid sequence at all the amino acid positions that correspond to positions 263, 265, 267, 269, 271, 491, 526 and 443 of SEQ ID NO:2, wherein the amino acid exchanges are M263V, N265K, T267N, M269A, S271Q, Q491R, K553R and D443G. Yet alternatively, mutations in the polynucleotide sequence of SEQ ID NO:1 cause amino acid exchanges within the encoded amino acid sequence at all the amino acid positions that correspond to positions 263, 265, 267, 269, 271, 491, 526 and 443 of SEQ ID NO:2, wherein the amino acid exchanges are M263V, N265K, T267N, M269A, S271Q, Q491R, R526H, K553R and D443G.

According to a further embodiment, the one or more mutations in the polynucleotide sequence of SEQ ID NO:1 cause one or more amino acid exchanges within the encoded amino acid sequence at the amino acid positions that correspond to positions 263, 265, 267, 269, 271, 356, 360, 362, 363, 491, 526 and 443 of SEQ ID NO:2, wherein the amino acid exchanges are M263V, N265K, T267N, M269A, S271Q, I356G, N360A, G362T, W363K, Q491R, R526H and D443G. In a preferred embodiment, mutations in the polynucleotide sequence of SEQ ID NO:1 cause amino acid exchanges within the encoded amino acid sequence at all the amino acid positions that correspond to positions 263, 265, 267, 269, 271, 356, 360, 362, 363, 491, 526 and 443 of SEQ ID NO:2, wherein the amino acid exchanges are M263V, N265K, T267N, M269A, S271Q, I356G, N360A, G362T, W363K, Q491R, R526H and D443G.

According to a preferred embodiment, a first subunit of the two subunits comprises the complete amino acid sequence encoded by the variant of SEQ ID NO:1 and a second subunit of the two subunits comprises a proteolytic fragment of the complete amino acid sequence encoded by the variant of SEQ ID NO:1.

In another aspect, the invention refers to a method for amplifying template nucleic acids comprising contacting the template nucleic acids with an RT of the invention. In one embodiment, the method is reverse transcription (RT) PCR.

In a further aspect, the present invention provides a kit comprising the RT of the invention and a buffer.

Another aspect of the invention relates to a polynucleotide encoding an RT of the invention. A further aspect of the invention relates to a vector comprising the polynucleotide according to the invention. In another aspect, the invention relates to transformed host cells comprising said vector.

In another aspect, the invention provides an RT obtainable by expression of the polynucleotide or the vector according to the invention in a host cell. In a preferred embodiment, the host cell is *E. coli*.

In yet another embodiment, the invention relates to a method of producing an RT of the invention comprising isolating the RT from the transformed host cell.

BRIEF DESCRIPTION OF THE DRAWINGS

The present disclosure will be more readily appreciated by reference to the following detailed description when being considered in connection with the accompanying drawings in which:

FIG. 1 shows the results of a thermal stability assay using different RTs that have been subjected to a preincubation step at the indicated temperatures prior to the RT reaction at 42° C.

DETAILED DESCRIPTION OF THE INVENTION

Definitions

Figure 2:
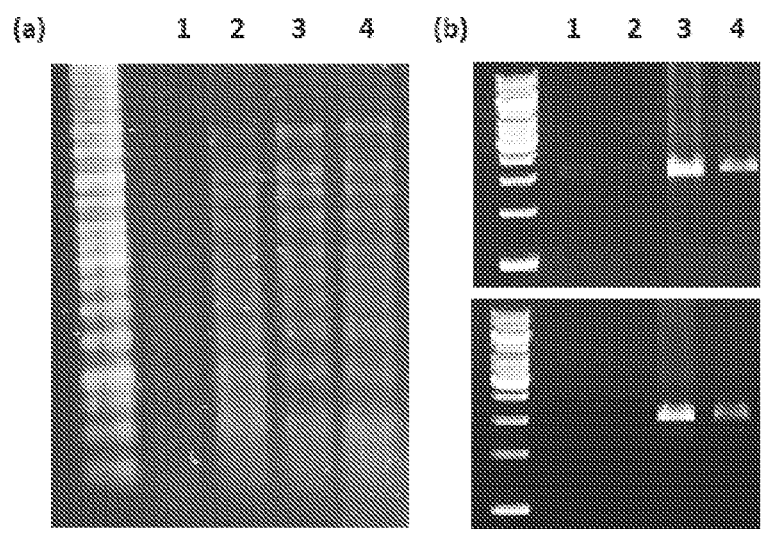
FIG. 2 depicts the results of a thermal stability assay measuring cDNA synthesis at elevated temperature using different RTs. Panel (a) shows the results of cDNA synthesis reactions at 50° C. Panel (b) shows the results of 2-step RT-PCR reactions where cDNA was generated at 50° C. (upper panel) and 60° C. (lower panel).

Unless defined otherwise, all technical and scientific terms used herein have the same meaning as commonly understood by one of ordinary skill in the art (e.g., in cell culture, molecular genetics, nucleic acid chemistry, hybridization techniques and biochemistry).

In practicing the present invention, many conventional techniques in molecular biology, microbiology, and recombinant DNA may be used. These techniques are well known and are explained in, for example, Current Protocols in Molecular Biology, Volumes I, II, and III, 1997 (F. M. Ausubel ed.); Sambrook et al., 1989, Molecular Cloning: A Laboratory Manual, Second Edition, Cold Spring Harbor Laboratory Press, Cold Spring Harbor, N.Y.; DNA Cloning: A Practical Approach, Volumes I and II, 1985 (D. N. Glover ed.); Oligonucleotide Synthesis, 1984 (M. L. Gait ed.); Nucleic Acid Hybridization, 1985 (Hames and Higgins); Transcription and Translation, 1984 (Hames and Higgins eds.); Animal Cell Culture, 1986 (R. I. Freshney ed.); Immobilized Cells and Enzymes, 1986 (IRL Press); Perbal, 1984, A Practical Guide to Molecular Cloning; the series, Methods In Enzymology (Academic Press, Inc.); Gene Transfer Vectors for Mammalian Cells, 1987 (J. H. Miller and M. P. Calos eds., Cold Spring Harbor Laboratory); and Methods in Enzymology Vol. 154 and Vol. 155 (Wu and Grossman, and Wu, eds., respectively).

As used herein, the term "comprising" is to be construed as encompassing both "including" and "consisting of", both meanings being specifically intended, and hence individually disclosed embodiments in accordance with the present invention.

The term "nucleic acid sequence", "nucleotide sequence" or "polynucleotide sequence" as used herein refers to an oligonucleotide, nucleotide or polynucleotide and fragments and portions thereof and to DNA or RNA of genomic or synthetic origin, which may be single or double stranded and represent the sense or antisense strand. The sequence may be a non-coding sequence, a coding sequence or a mixture of both.

A "variant" of a polynucleotide sequence (e.g., RNA or DNA) comprises one or more mutations within the polynucleotide sequence relative to another polynucleotide sequence wherein one or more nucleic acid residues are inserted into, deleted from and/or substituted into the nucleic acid sequence. Said one or more mutations can cause one or more amino acid exchanges within the amino acid sequence the variant encodes for as compared to another amino acid sequence (i.e. a "non-silent mutation"). Variants also include nucleic acid sequences wherein one or more codons have been replaced by their synonyms which does not cause an amino acid exchange and is thus called a "silent mutation".

The term "identity" refers to a relationship between the sequences of two or more polypeptide molecules or two or more nucleic acid molecules, as determined by aligning and comparing the sequences. "Percent identity" means the percent of identical residues between the amino acids or nucleotides in the compared molecules and is calculated based on the size of the smallest of the molecules being compared. For these calculations, gaps in alignments (if any) are preferably addressed by a particular mathematical model or computer program (i.e., an "algorithm"). Methods that can be used to calculate the identity of the aligned nucleic acids or polypeptides include those described in Computational Molecular Biology, (Lesk, A. M., ed.), 1988, New York: Oxford University Press; Biocomputing Informatics and Genome Projects, (Smith, D. W., ed.), 1993, New York: Academic Press; Computer Analysis of Sequence Data, Part I, (Griffin, A. M., and Griffin, H. G., eds.), 1994, New Jersey: Humana Press; von Heinje, G., 1987, Sequence Analysis in Molecular Biology, New York: Academic Press; Sequence Analysis Primer, (Gribskov, M. and Devereux, J., eds.), 1991, New York: M. Stockton Press; and Carillo et al, 1988, SI AM J. Applied Math. 48: 1073.

In calculating percent identity, the sequences being compared are typically aligned in a way that gives the largest match between the sequences. Computer programs that can be used to determine percent identity are discussed, e.g., by Pearson (Pearson, 2013, Curr. Protoc. Bioinform. 42:3.1.1☐3.1.8). Such computer algorithms are used to align the two polypeptides or polynucleotides for which the percent sequence identity is to be determined. The sequences are aligned for optimal matching of their respective amino acid or nucleotide (the "matched span", as determined by the algorithm).

Certain alignment schemes for aligning two sequences may result in matching of only a short region of the two sequences, and this small aligned region may have very high sequence identity even though there is no significant relationship between the two full-length sequences. Accordingly, the selected alignment method can be adjusted if so desired to result in an alignment that spans at least 50 or other number of contiguous nucleotides or amino acids.

The nucleic acid sequences of the present invention can be prepared using standard techniques well known to one of skill in the art. The term "encoding" or "coding" refers to the inherent property of specific sequences of nucleotides in a nucleic acid, such as a gene in chromosome or an mRNA, to serve as templates for synthesis of other polymers and macromolecules in biological processes having a defined sequence of nucleotides (i.e., rRNA, tRNA, other RNA molecules) or amino acids and the biological properties resulting therefrom. Thus a gene encodes a protein, if transcription and translation of mRNA produced by that gene produces the protein in a cell or other biological system. Both the coding strand, the nucleotide sequence of which is identical to the mRNA sequence and is usually provided in sequence listings, and non-coding strand, used as the template for the transcription, of a gene or cDNA can be referred to as encoding the protein or other product of that gene or cDNA. A nucleic acid that encodes a protein includes any nucleic acids that have different nucleotide sequences but encode the same amino acid sequence of the protein due to the degeneracy of the genetic code. Nucleic acids and nucleotide sequences that encode proteins may include introns.

The term "polypeptide" is used interchangeably with "amino acid sequence" or "protein" and refers to polymers of amino acids of any length. These terms also include proteins that are post-translationally modified through reactions that include, but are not limited to, glycosylation, acetylation, phosphorylation or protein processing. Modifications and changes, for example fusions to other proteins, amino acid sequence substitutions, deletions or insertions, can be made in the structure of a polypeptide while the molecule maintains its biological functional activity. For example certain amino acid sequence substitutions can be made in a polypeptide or its underlying nucleic acid coding sequence and a protein can be obtained with like properties. Amino acid modifications can be prepared for example by performing site-specific mutagenesis or polymerase chain reaction mediated mutagenesis on its underlying nucleic acid sequence.

The term "expressed" as used herein refers to transcription and/or translation of a heterologous nucleic acid sequence within a host cell. "Production" would involve both transcription and translation. The level of expression in a host cell may be determined on the basis of either the amount of corresponding mRNA that is present in the cell, and production would be based on the amount of the desired polypeptide. For example, mRNA transcribed from a selected sequence can be quantitated by Northern blot hybridization, ribonuclease RNA protection, in situ hybridization to cellular RNA or by PCR (see Sambrook et al. (1989), supra; Ausubel et al. (1994 updated), supra). Proteins encoded by a selected sequence can be quantitated by various methods, e.g., by ELISA, by Western blotting, by radioimmunoassays, by immunoprecipitation, by assaying for the biological activity of the protein, or by immunostaining of the protein followed by FACS analysis PCR (see Sambrook et al. (1989), supra; Ausubel et al. (1994 updated), supra).

The term "PCR" refers to polymerase chain reaction, which is a standard method in molecular biology for DNA amplification.

"RT-PCR" relates to reverse transcription polymerase chain reaction, a variant of PCR commonly used for the detection and quantification of RNA. RT-PCR comprises two steps, synthesis of complementary DNA (cDNA) from RNA by reverse transcription and amplification of the generated cDNA by PCR. Variants of RT-PCR include quantitative RT-PCR (RT-qPCR), real-time RT-PCR, digital RT-PCR (dRT-PCR) or digital droplet RT-PCR (ddRT-PCR).

In the following, the invention will be explained in more detail with reference to the accompanying figures. It will be obvious for a person skilled in the art that these embodiments and items only depict examples of a plurality of possibilities. Hence, the embodiments shown here should not be understood to form a limitation of these features and configurations. Any possible combination and configuration of the described features can be chosen according to the scope of the invention.

Polymerases/Enzymes

Equine infectious anemia virus reverse transcriptases (EIAV RTs) are active in vivo as a heterodimer comprising subunits of 66 kDa and 51 kDa derived from a single open reading frame. The smaller subunit of 51 kDa is a proteolytic fragment of the bigger 66 kDa subunit. Expression of the open reading frame of SEQ ID NO:1 in *E. coli* gives rise to both the 66 kDa and the 51 kDa subunits that can form homodimers (i.e., p66/p66 and p51/p51) and heterodimers (i.e., p66/p51). Some commercial preparations of RTs are mixtures of the homodimers and heterodimers. While both types of dimers are active in DNA synthesis, the heterodimer presents with higher stability and processivity than the homodimers.

A preferred embodiment of the RT according to the invention thus is an enzyme preparation being enriched for heterodimers. Enrichment can be done through any method known to the skilled person, for example chromatography including Heparin, hydrophobic interaction chromatography (HIC), and ion exchanges. An enzyme preparation is enriched for heterodimers if the content of heterodimers is at least 25% higher as compared to the pre-enrichment content of heterodimers in the enzyme preparation. In some embodiments of this aspect of the invention, the content of heterodimers is enriched by at least 30% as compared to the pre-enrichment content of heterodimers in the enzyme preparation. In another embodiment, the content of heterodimers is enriched by at least 50% as compared to the pre-enrichment content of heterodimers in the enzyme preparation. In a preferred embodiment of this aspect of the invention, the content of heterodimers is enriched by at least 75% as compared to the pre-enrichment content of heterodimers in the enzyme preparation. In a more preferred embodiment of this aspect of the invention, the content of heterodimers is enriched by at least 100% as compared to the pre-enrichment content of heterodimers in the enzyme preparation. In a particularly preferred embodiment of this aspect of the invention, the heterodimer is purified to apparent homogeneity.

In a first aspect, the present invention provides a reverse transcriptase (RT) comprising two subunits, wherein the two subunits are each encoded by a variant of the polynucleotide sequence of SEQ ID NO:1, wherein the amino acid sequence encoded by the variant is at least 90% identical to the amino acid sequence of SEQ ID NO:2 or a fragment thereof, and wherein the variant comprises one or more mutations in the polynucleotide sequence of SEQ ID NO:1 causing one or more amino acid exchanges relative to the amino acid sequence of SEQ ID NO:2 in the minor groove binding track (MGBT) of the RT's thumb domain and/or the RT's connection domain (CD).

The variant of SEQ ID NO:1 can comprise an arbitrary number of codons that have been replaced by their synonyms (see Table 1) which does not cause an amino acid exchange within the amino acid sequence relative to SEQ ID NO:2. Additionally, the variant comprises at least one mutation that causes an amino acid exchange relative to the amino acid sequence of SEQ ID NO:2. In some embodiments, the variant comprises at least two mutations that cause amino acid exchanges relative to the amino acid sequence of SEQ ID NO:2. In another embodiment, the variant comprises at least three mutations that cause amino acid exchanges relative to the amino acid sequence of SEQ ID NO:2. In another embodiment, the variant comprises at least four mutations that cause amino acid exchanges relative to the amino acid sequence of SEQ ID NO:2. In another embodiment, the variant comprises at least five mutations that cause amino acid exchanges relative to the amino acid sequence of SEQ ID NO:2. In another embodiment, the variant comprises at least six mutations that cause amino acid exchanges relative to the amino acid sequence of SEQ ID NO:2. In another embodiment, the variant comprises at least eight mutations that cause amino acid exchanges relative to the amino acid sequence of SEQ ID NO:2. In another embodiment, the variant comprises at least ten mutations that cause amino acid exchanges relative to the amino acid sequence of SEQ ID NO:2.

TABLE 1

Genetic code

| # | Amino acid | codon |
|---|---|---|
| | Start | AUG |
| 1 | Met | AUG |
| 1 | Trp | UGG |
| 1 | Sec | (UGA) |
| 1 | Pyl | (UAG) |
| 2 | Tyr | UAU |
| 2 | Phe | UUU |
| 2 | Cys | UGU |
| 2 | Asn | AAU |
| 2 | Asp | GAU |
| 2 | Gln | CAA |
| 2 | Glu | GAA |
| 2 | His | CAU CAC |
| 2 | Lys | AAA AAG |
| 3 | Ile | AUU AUC AUA |
| 4 | Gly | GGU GGC GGA GGG |
| 4 | Ala | GCU GCC GCA GCG |
| 4 | Val | GUU GUC GUA GUG |
| 4 | Thr | ACU ACC ACA ACG |
| 4 | Pro | CCU CCC CCA CCG |
| 6 | Leu | CUU CUC CUA CUG UUA |
| 6 | Ser | UCU UCC UCA UCG AGU |
| 6 | Arg | CGU CGC CGA CGG AGA |
| 3 | Stop | UAA UAG UGA |

In some embodiments according to this aspect of the invention, the variant of SEQ ID NO:1 comprises one mutation that causes an amino acid exchange relative to the amino acid sequence of SEQ ID NO:2. In another embodiment, the variant comprises two mutations that cause amino acid exchanges relative to the amino acid sequence of SEQ ID NO:2. In another embodiment, the variant comprises three mutations that cause amino acid exchanges relative to the amino acid sequence of SEQ ID NO:2. In another embodiment, the variant comprises four mutations that cause amino acid exchanges relative to the amino acid sequence of SEQ ID NO:2. In another embodiment, the variant comprises five mutations that cause amino acid exchanges relative to the amino acid sequence of SEQ ID NO:2. In another embodiment, the variant comprises six mutations that cause amino acid exchanges relative to the amino acid sequence of SEQ ID NO:2. In another embodiment, the variant comprises eight mutations that cause amino acid exchanges relative to the amino acid sequence of SEQ ID NO:2. In another embodiment, the variant comprises ten mutations that cause amino acid exchanges relative to the amino acid sequence of SEQ ID NO:2. In another embodiment, the variant comprises twelve mutations that cause amino acid exchanges relative to the amino acid sequence of SEQ ID NO:2.

The one or more amino acid exchanges relative to the amino acid sequence of SEQ ID NO:2 can locate to the minor groove binding track (MGBT) of the RT's thumb domain spanning amino acid residues 255-298 of SEQ ID NO:2, the RT's connection domain (CD) spanning amino acid residues 320-414 of SEQ ID NO:2, and/or the RT's RNase H domain spanning amino acid residues 438-553 of SEQ ID NO:2. In some embodiments according to this aspect of the invention, the at least one amino acid exchange relative to the amino acid sequence of SEQ ID NO:2 locates to the MGBT of the RT's thumb domain. In other embodiments according to this aspect of the invention, the at least one amino acid exchange relative to the amino acid sequence of SEQ ID NO:2 locates to the RT's CD. In further embodiments according to this aspect of the invention, the at least one amino acid exchange relative to the amino acid sequence of SEQ ID NO:2 locates to the RT's RNase H domain. In preferred embodiments, the at least two amino acid exchanges relative to the amino acid sequence of SEQ ID NO:2 locate to the MGBT of the RT's thumb domain and the RT's CD. In another preferred embodiments, the at least two amino acid exchanges relative to the amino acid sequence of SEQ ID NO:2 locate to the MGBT of the RT's thumb domain and the RT's RNase H domain. In particularly preferred embodiments, the at least three amino acid exchanges relative to the amino acid sequence of SEQ ID NO:2 locate to the MGBT of the RT's thumb domain, the RT's RNase H domain and the RT's CD.

In some embodiments according to this aspect of the invention, the variant of SEQ ID NO:1 comprises one or more mutations that cause one amino acid exchange relative to the amino acid sequence of SEQ ID NO:2. This one amino acid exchange relative to the amino acid sequence of SEQ ID NO:2 can locate to the minor groove binding track (MGBT) of the RT's thumb domain spanning amino acid residues 255-298 of SEQ ID NO:2, the RT's connection domain (CD) spanning amino acid residues 320-414 of SEQ ID NO:2, and/or the RT's RNase H domain spanning amino acid residues 438-553 of SEQ ID NO:2. In certain embodiments, this one amino acid exchange relative to the amino acid sequence of SEQ ID NO:2 locates to the MGBT of the RT's thumb domain. In other embodiments, this one amino acid exchange relative to the amino acid sequence of SEQ ID NO:2 locates to the RT's CD. In further embodiments, this one amino acid exchange relative to the amino acid sequence of SEQ ID NO:2 locates to the RT's RNase H domain. In preferred embodiments, the variant comprises mutations that cause two amino acid exchanges relative to the amino acid sequence of SEQ ID NO:2. These two amino acid exchanges relative to the amino acid sequence of SEQ ID NO:2 locate to the MGBT of the RT's thumb domain and the RT's CD. In another preferred embodiments, these two amino acid exchanges relative to the amino acid sequence of SEQ ID NO:2 locate to the MGBT of the RT's thumb domain and the RT's RNase H domain. In particularly preferred embodiments, the variant comprises mutations that cause three amino acid exchanges relative to the amino acid sequence of SEQ ID NO:2. These three amino acid exchanges relative to the amino acid sequence of SEQ ID NO:2 locate to the MGBT of the RT's thumb domain, the RT's RNase H domain and the RT's CD.

In some embodiments according to this aspect of the invention, the amino acid sequence encoded by the variant of SEQ ID NO:1 is at least 90% identical to the amino acid sequence of SEQ ID NO:2 or a fragment thereof. In other embodiments, the amino acid sequence encoded by the variant is at least 95% identical to the amino acid sequence of SEQ ID NO:2 or a fragment thereof. In preferred embodiments according to this aspect of the invention, the amino acid sequence encoded by the variant is at least 97% identical to the amino acid sequence of SEQ ID NO:2 or a fragment thereof. An amino acid sequence that is at least 90%, at least 95% or at least 97% identical to the amino acid sequence of SEQ ID NO:2 or a fragment thereof retains the biological function of the amino acid sequence of SEQ ID NO:2 or a fragment thereof. More specifically, an amino acid sequence that is at least 90%, at least 95% or at least 97% identical to the amino acid sequence of SEQ ID NO:2 or a fragment thereof retains the reverse transcriptase activity of EIAV-RT.

According to one embodiment, the one or more amino acid exchanges according to this aspect of the invention can be caused within the encoded amino acid sequence at the amino acid positions that correspond to positions 263, 265, 267, 269, and 271 of SEQ ID NO:2, wherein the amino acid exchanges are M263V, N265K, T267N, M269A, and S271Q. Preferably, the EIAV RT comprises at least two of said amino acid exchanges within its MGBT. More preferably, the EIAV RT comprises at least three of said amino acid exchanges within its MGBT. In some further embodiments, the EIAV RT comprises two of said amino acid exchanges within its MGBT. More preferably, the EIAV RT comprises three of said amino acid exchanges within its MGBT. Particularly preferred, the EIAV RT comprises all of said amino acid exchanges within its MGBT.

In addition or alternatively to the at least one amino acid exchange within the RT's MGBT, the one or more amino acid exchanges can be caused within the encoded amino acid sequence at the amino acid positions that correspond to positions 356, 360, 362, and 363 of SEQ ID NO:2, wherein the amino acid exchanges are I356G or I356D or I356N, N360A, G362T or G362N, and W363K or W363N or W363I, preferably I356G, N360A, G362T and W363K. Preferably, the EIAV RT comprises at least two of said amino acid exchanges within its CD. More preferably, the EIAV RT comprises at least three of said amino acid exchanges within its CD. In some further embodiments, the EIAV RT comprises two of said amino acid exchanges within its CD. More preferably, the EIAV RT comprises three of said amino acid exchanges within its CD. Particularly preferred, the EIAV RT comprises all of said amino acid exchanges within its CD.

In addition or alternatively to the at least one amino acid exchange within the RT's MGBT, the one or more amino acid exchanges can be caused within the encoded amino acid sequence at the amino acid positions that correspond to positions 443, 470, 476, 491, 526 and 553 of SEQ ID NO:2, wherein the amino acid exchanges are D443G, V470F, E476Q, Q491R, R526H and K553R. According to one embodiment, the EIAV RT comprises an amino acid exchange corresponding to position D443G and/or E476Q of SEQ ID NO:2. According to one embodiment, the EIAV RT comprises one amino acid exchange corresponding to position D443G of SEQ ID NO:2. This EIAV RT has an amino acid sequence of SEQ ID NO:4 that is encoded by the nucleic acid sequence of SEQ ID NO:3 or a synonymous variant thereof. According to another embodiment, the EIAV RT comprises two amino acid exchanges corresponding to positions D443G and E476Q of SEQ ID NO:2. Said EIAV RT has an amino acid sequence of SEQ ID NO:6 that is encoded by the nucleic acid sequence of SEQ ID NO:5 or a synonymous variant thereof. In a preferred embodiment, one of the amino acid exchanges is D443G. In other embodiments, the EIAV RT comprises at least two of the aforementioned amino acid exchanges within its RNase H domain. According to further embodiments, the EIAV RT comprises at least three of said amino acid exchanges within its RNase H domain. In some further embodiments, the EIAV RT comprises two of the aforementioned amino acid exchanges within its RNase H domain. According to further embodiments, the EIAV RT comprises three of said amino acid exchanges within its RNase H domain. Particularly preferred, the EIAV RT comprises the amino acid exchanges D443G, Q491R, and R526H.

In some embodiments according to this aspect of the invention, the one or more mutations in the polynucleotide sequence of SEQ ID NO:1 cause one or more amino acid exchanges within the encoded amino acid sequence at the amino acid positions that correspond to positions 263, 265, 267, 269, 271 and 443 of SEQ ID NO:2, wherein the amino acid exchanges are M263V, N265K, T267N, M269A, S271Q and D443G. Preferably, the EIAV RT comprises at least two of the aforementioned amino acid exchanges, wherein at least one of said amino acid exchanges locates to the RNase H domain and at least one of said amino acid exchanges locates to the MGBT. More preferably, the EIAV RT comprises at least three of the aforementioned amino acid exchanges, wherein at least one of said amino acid exchanges locates to the RNase H domain and at least two of said amino acid exchanges locate to the MGBT. According to another preferred embodiment, the EIAV RT comprises at least four of the aforementioned amino acid exchanges, wherein at least one of said amino acid exchanges locates to the RNase H domain and at least three of said amino acid exchanges locate to the MGBT. According to a further preferred embodiment, the EIAV RT comprises at least five of the aforementioned amino acid exchanges, wherein at least one of said amino acid exchanges locates to the RNase H domain and at least four of said amino acid exchanges locate to the MGBT. In some further embodiments, the EIAV RT comprises two of the aforementioned amino acid exchanges, wherein one of said amino acid exchanges locates to the RNase H domain and one of said amino acid exchanges locates to the MGBT. Preferably, the EIAV RT comprises three of the aforementioned amino acid exchanges, wherein one of said amino acid exchanges locates to the RNase H domain and two of said amino acid exchanges locate to the MGBT. According to another preferred embodiment, the EIAV RT comprises four of the aforementioned amino acid exchanges, wherein one of said amino acid exchanges locates to the RNase H domain and three of said amino acid exchanges locate to the MGBT. According to a further preferred embodiment, the EIAV RT comprises five of the aforementioned amino acid exchanges, wherein one of said amino acid exchanges locates to the RNase H domain and four of said amino acid exchanges locate to the MGBT. Particularly preferred, the EIAV RT comprises all of the aforementioned amino acid exchanges. The latter EIAV RT has an amino acid sequence of SEQ ID NO:8 that is encoded by the nucleic acid sequence of SEQ ID NO:7 or a synonymous variant thereof.

In further embodiments according to this aspect of the invention, the one or more mutations in the polynucleotide sequence of SEQ ID NO:1 cause one or more amino acid exchanges within the encoded amino acid sequence at the amino acid positions that correspond to positions 263, 265, 267, 269, 271, 356, 360, 362, 363 and 443 of SEQ ID NO:2, wherein the amino acid exchanges are M263V, N265K, T267N, M269A, S271Q, I356G, N360A, G362T, W363K and D443G. Preferably, the EIAV RT comprises at least three of the aforementioned amino acid exchanges, wherein at least one of said amino acid exchanges locates to the RNase H domain, at least one of said amino acid exchanges locates to the MGBT and at least one of said amino acid exchanges locates to the CD. According to another preferred embodiment, the EIAV RT comprises at least four of the aforementioned amino acid exchanges, wherein at least one of said amino acid exchanges locates to the RNase H domain, at least one of said amino acid exchanges locates to the MGBT and at least one of said amino acid exchanges locates to the CD. According to further preferred embodiments, the EIAV RT comprises at least five of the aforementioned amino acid exchanges, wherein at least one of said amino acid exchanges locates to the RNase H domain, at least two of said amino acid exchanges locate to the MGBT and at least two of said amino acid exchanges locate to the CD. According to other preferred embodiments, the EIAV RT comprises at least six of the aforementioned amino acid exchanges, wherein at least one of said amino acid exchanges locates to the RNase H domain, at least two of said amino acid exchanges locate to the MGBT and at least two of said amino acid exchanges locate to the CD. According to more preferred embodiments, the EIAV RT comprises at least seven of the aforementioned amino acid exchanges, wherein at least one of said amino acid exchanges locates to the RNase H domain, at least three of said amino acid exchanges locate to the MGBT and at least three of said amino acid exchanges locate to the CD. According to further more preferred embodiments, the EIAV RT comprises at least eight of the aforementioned amino acid exchanges, wherein at least one of said amino acid exchanges locates to the RNase H domain, at least three of said amino acid exchanges locate to the MGBT and at least three of said amino acid exchanges locate to the CD. According to other more preferred embodiments, the EIAV RT comprises at least nine of the aforementioned amino acid exchanges, wherein at least one of said amino acid exchanges locates to the RNase H domain, at least four of said amino acid exchanges locate to the MGBT and at least four of said amino acid exchanges locate to the CD. In some further embodiments, the EIAV RT comprises three of the aforementioned amino acid exchanges, wherein one of said amino acid exchanges locates to the RNase H domain, one of said amino acid exchanges locates to the MGBT and one of said amino acid exchanges locates to the CD. According to another embodiment, the EIAV RT comprises four of the aforementioned amino acid exchanges, wherein one of said amino acid exchanges locates to the RNase H domain and one or two of said amino acid exchanges locate to the MGBT and the CD respectively. According to further embodiments, the EIAV RT comprises five of the aforementioned amino acid exchanges, wherein one of said amino acid exchanges locates to the RNase H domain, two of said amino acid exchanges locate to the MGBT and two of said amino acid exchanges locate to the CD. According to other embodiments, the EIAV RT comprises six of the aforementioned amino acid exchanges, wherein one of said amino acid exchanges locates to the RNase H domain and two or three of said amino acid exchanges locate to the MGBT and and the CD respectively. According to more preferred embodiments, the EIAV RT comprises seven of the aforementioned amino acid exchanges, wherein one of said amino acid exchanges locates to the RNase H domain, three of said amino acid exchanges locate to the MGBT and three of said amino acid exchanges locate to the CD. According to further more preferred embodiments, the EIAV RT comprises eight of the aforementioned amino acid exchanges, wherein one of said amino acid exchanges locates to the RNase H domain and three or four of said amino acid exchanges locate to the MGBT and the CD respectively. According to other more preferred embodiments, the EIAV RT comprises nine of the aforementioned amino acid exchanges, wherein one of said amino acid exchanges locates to the RNase H domain, four of said amino acid exchanges locate to the MGBT and four of said amino acid exchanges locate to the CD. Particularly preferred, the EIAV RT comprises all of the aforementioned amino acid exchanges. The latter EIAV RT has an amino acid sequence of SEQ ID NO:10 that is encoded by the nucleic acid sequence of SEQ ID NO:9 or a synonymous variant thereof.

According to another embodiment, the mutations in the polynucleotide sequence of SEQ ID NO:1 cause amino acid exchanges within the encoded amino acid sequence at all the amino acid positions that correspond to positions 263, 265, 267, 269, 271, 356, 360, 362, 363 and 443 of SEQ ID NO:2, wherein the amino acid exchanges are M263V, N265K, T267N, M269A, S271Q, I356G, N360A, G362T, W363N and D443G.

According to another embodiment, the mutations in the polynucleotide sequence of SEQ ID NO:1 cause amino acid exchanges within the encoded amino acid sequence at all the amino acid positions that correspond to positions 263, 265, 267, 269, 271, 356, 360, 362, 363 and 443 of SEQ ID NO:2, wherein the amino acid exchanges are M263V, N265K, T267N, M269A, S271Q, I356G, N360A, G362T, W363N and D443G.

According to another embodiment, the mutations in the polynucleotide sequence of SEQ ID NO:1 cause amino acid exchanges within the encoded amino acid sequence at all the amino acid positions that correspond to positions 263, 265, 267, 269, 271, 356, 360, 362, 363 and 443 of SEQ ID NO:2, wherein the amino acid exchanges are M263V, N265K, T267N, M269A, S271Q, I356D, N360A, G362T, W363K and D443G.

According to another embodiment, the mutations in the polynucleotide sequence of SEQ ID NO:1 cause amino acid exchanges within the encoded amino acid sequence at all the amino acid positions that correspond to positions 263, 265, 267, 269, 271, 356, 360, 362, 363 and 443 of SEQ ID NO:2, wherein the amino acid exchanges are M263V, N265K, T267N, M269A, S271Q, I356N, N360A, G362N, W363I and D443G.

According to another embodiment, the mutations in the polynucleotide sequence of SEQ ID NO:1 cause amino acid exchanges within the encoded amino acid sequence at all the amino acid positions that correspond to positions 263, 265, 267, 269, 271, 443, 491 and 526 of SEQ ID NO:2, wherein the amino acid exchanges are M263V, N265K, T267N, M269A, S271Q, D443G, Q491R and R526H. Said EIAV RT has an amino acid sequence of SEQ ID NO:12 that is encoded by the nucleic acid sequence of SEQ ID NO:11 or a synonymous variant thereof.

According to another embodiment, the mutations in the polynucleotide sequence of SEQ ID NO:1 cause amino acid exchanges within the encoded amino acid sequence at all the amino acid positions that correspond to positions 263, 265, 267, 269, 271, 443, 491 and 526 of SEQ ID NO:2, wherein the amino acid exchanges are M263V, N265K, T267N, M269A, S271Q, D443G, Q491R and K553R.

According to another embodiment, the mutations in the polynucleotide sequence of SEQ ID NO:1 cause amino acid exchanges within the encoded amino acid sequence at all the amino acid positions that correspond to positions 263, 265, 267, 269, 271, 443, 470, 491, 526 and 553 of SEQ ID NO:2, wherein the amino acid exchanges are M263V, N265K, T267N, M269A, S271Q, D443G, V470F, Q491R, R526H and K553R.

According to a further embodiment, the mutations in the polynucleotide sequence of SEQ ID NO:1 cause amino acid exchanges within the encoded amino acid sequence at all the amino acid positions that correspond to positions 263, 265, 267, 269, 271, 356, 360, 362, 363, 443, 491 and 526 of SEQ ID NO:2, wherein the amino acid exchanges are M263V, N265K, T267N, M269A, S271Q, I356G, N360A, G362T, W363K, D443G, Q491R and R526H. Said EIAV RT has an amino acid sequence of SEQ ID NO:14 that is encoded by the nucleic acid sequence of SEQ ID NO:13 or a synonymous variant thereof.

The following Table 2 summarizes the amino acid sequences of preferred embodiments according to the present invention and indicates one nucleic acid sequence encoding it. The skilled person knows that the amino acid sequences listed can also be encoded by nucleic acid sequences synonymous to those indicated in Table 2. The present invention also encompasses any of said synonymous nucleic acid sequences.

TABLE 2

Preferred embodiments and their nucleic/amino acid sequences

| Variant | Nucleic acid sequence | Amino acid sequence |
|---|---|---|
| EIAV RT WT | SEQ ID NO: 1 | SEQ ID NO: 2 |
| EIAV RT V1 | SEQ ID NO: 3 | SEQ ID NO: 4 |
| EIAV RT V2 | SEQ ID NO: 5 | SEQ ID NO: 6 |
| EIAV RT V3 | SEQ ID NO: 7 | SEQ ID NO: 8 |
| EIAV RT V4 | SEQ ID NO: 9 | SEQ ID NO: 10 |
| EIAV RT V5 | SEQ ID NO: 11 | SEQ ID NO: 12 |
| EIAV RT V6 | SEQ ID NO: 13 | SEQ ID NO: 14 |
| V4 variant W363N | | SEQ ID NO: 15 |
| V4 variant I356D | | SEQ ID NO: 16 |
| V4 variant I356N/G362N/W363I | | SEQ ID NO: 17 |
| V5 variant R526R/K553R | | SEQ ID NO: 18 |
| V5 variant V470F/K553R | | SEQ ID NO: 19 |

The EIAV RT according to the invention comprises two subunits that are both encoded by a variant of the polynucleotide sequence of SEQ ID NO: 1. Variants according to the invention are described in more detail herein above. Preferably, the RT is a heterodimer. According to some embodiments, a first subunit of the two subunits comprises the complete amino acid sequence encoded by the variant and a second subunit of the two subunits comprises a proteolytic fragment of the complete amino acid sequence encoded by the variant, i.e. a proteolytic fragment of the first subunit. The first subunit has a molecular weight of 66 kDa and the second subunit has a molecular weight of 51 kDa. Expression of the open reading frame of SEQ ID NO:1 in a host cell such as E. coli gives rise to both the 66 kD and the 51 kD subunits that can form homodimers (i.e., p66/p66 and p51/p51) and heterodimers (i.e., p66/p51). Some commercial preparations of RTs are mixtures of the homo- and heterodimers. While both types of dimers are active in DNA synthesis, the heterodimer presents with higher stability and processivity than the homodimers. Thus, in a preferred embodiment, the heterodimeric form of EIAV RT is purified to homogeneity.

In another aspect, the invention provides an RT obtainable by expression of the variant of the polynucleotide sequence of SEQ ID NO:1 or a vector comprising said variant in a host cell. Host cells that can be used to produce the EIAV RT according to the invention are mammalian cells, insect cells, yeast cells or bacterial cells. In a preferred embodiment, the host cells are mammalian cells such as HEK 293 or CHO cells or bacterial cells such as E. coli. The preferred host cells are E. coli.

Another aspect of the invention relates to a polynucleotide encoding an RT of the invention. Said polynucleotide is a variant of the polynucleotide sequence of SEQ ID NO:1 as described in more detail hereinabove. A further aspect of the invention relates to a vector comprising the polynucleotide according to the invention. Said polynucleotide is a variant of the polynucleotide sequence of SEQ ID NO:1 as described in more detail hereinabove. In another aspect, the invention relates to transformed host cells comprising said vector.

In yet another embodiment, the invention relates to a method of producing an RT of the invention comprising isolating the RT from the transformed host cell.

This invention thus provides novel engineered reverse transcriptase enzymes that afford beneficial improvements in thermal stability, processivity and thus length of cDNAs synthesized using an RNA template, cDNA yields and elimination of secondary enzymatic activity, i.e. RNase H activity. These improvements were incorporated into the parental (EIAV RT) molecule by directed mutagenesis of amino acid residues residing in thumb, connection, and/or RNase H domains. These mutations collectively eliminate RNase H activity and increase RT activity at elevated temperature and were identified from both rational design and random mutagenesis followed by screening. Combining these mutations allows significant improvement in performance including the capability to synthesize cDNAs of greater than 12 kb in length at the temperatures up to 65° C. and enables superior performance with even the most challenging RNA samples.

Methods

In another aspect, the present invention refers to methods for amplifying template nucleic acids comprising contacting the template nucleic acids with an RT according to the invention.

Template nucleic acids according to the present invention may be any type of nucleic acids, such as RNA, DNA, or RNA:DNA hybrids. Template nucleic acids may either be artificially produced (e.g. by molecular or enzymatic manipulations or by synthesis) or may be a naturally occurring DNA or RNA. In some preferred embodiments, the template nucleic acids are RNA sequences, such as transcription products, RNA viruses, or rRNA.

In some embodiments, the method referred to herein is RT-PCR. RT-PCR may be quantitative RT-PCR (RT-qPCR), real-time RT-PCR, digital RT-PCR (dRT-PCR) or digital droplet RT-PCR (ddRT-PCR).

In some preferred embodiments, the method of the invention comprises the steps of
  a) generating cDNA using a RT of the invention; and
  b) amplifying the generated cDNA using a DNA polymerase such as a Taq DNA polymerase.

In some embodiments, serum albumin is added during amplification, preferably recombinant human at a concentration of 1 mg/ml.

In some embodiments, the method of the invention further comprises detecting and/or quantifying the amplified nucleic acids. Quantification/detection of amplified nucleic acids may be performed, e.g., using non-sequence-specific fluorescent dyes (e.g., SYBR® Green, EvaGreen®) that intercalate into double-stranded DNA molecules in a sequence non-specific manner, or sequence-specific DNA probes (e.g., oligonucleotides labelled with fluorescent reporters) that permit detection only after hybridization with the DNA targets, synthesis-dependent hydrolysis or after incorporation into PCR products.

Kits

Reagents necessary to perform the method of the invention may be comprised in kits.

In some embodiments, the invention relates to kits for amplifying template nucleic acids, wherein the kit comprises an RT of the invention and a buffer. Optionally, the kit additionally comprises Taq DNA polymerase and/or serum albumin. Buffers comprised in the kit may be conventional buffers containing magnesium.

EXAMPLES

The invention is illustrated in the following examples.

Example 1: Expression and Purification of EIAV RT

Figure 1:
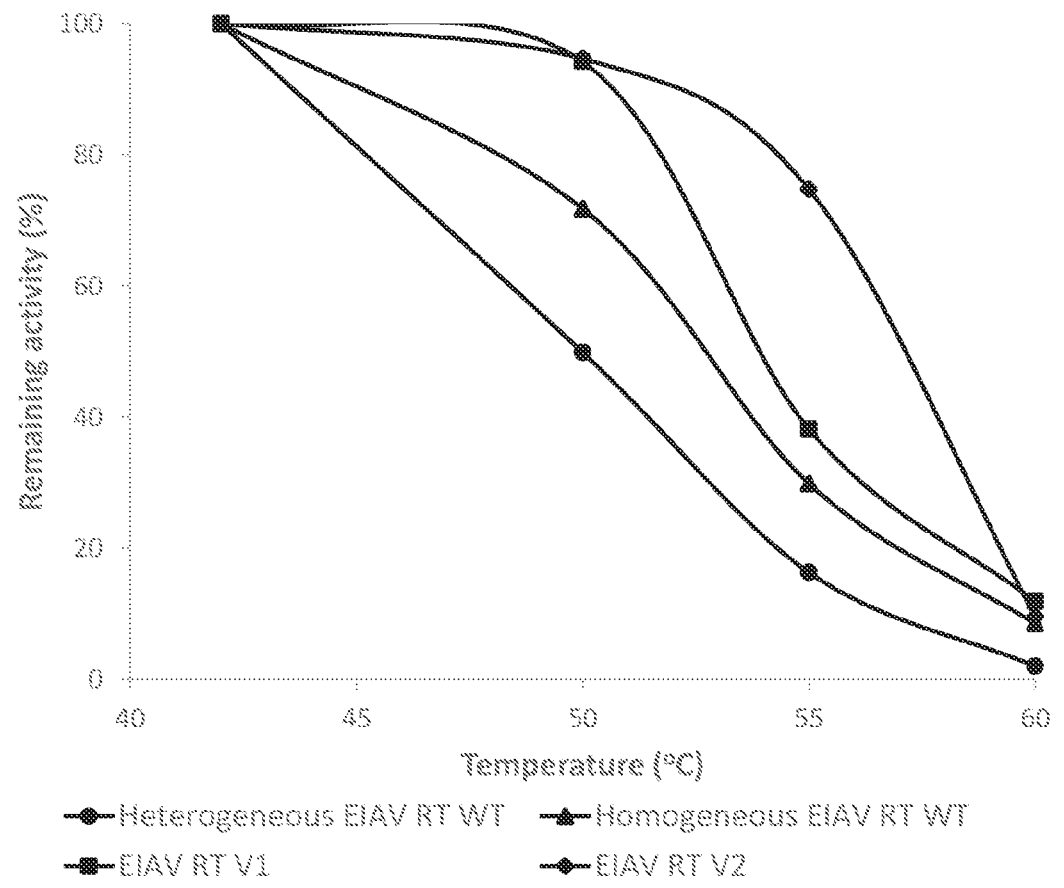

The open reading frame of SEQ ID NO:1 or a variant thereof was expressed in *E. coli* which gives rise to a 66 kDa polypeptide and a proteolytically processed fragment thereof, i.e. a 51 kDa polypeptide. The 66 kDa polypeptide has an amino acid sequence that is at least 90% identical to the amino acid sequence of SEQ ID NO:2. The 66 kDa and 51 kDa polypeptides form homodimers (i.e., p66/p66 and p51/p51) and heterodimers (i.e., p66/p51). In one preparation, referred to as the "homogeneous" preparation, the heterodimeric form (p66/p51) was separated from either of the homodimeric forms (p66/p66 and p51/p51) through multiple rounds of chromatography steps including heparin, hydrophobic interaction, and ion exchange chromatography; in a second preparation, referred to as the "heterogeneous" preparation, the homodimers and heterodimers were present in approximately equal amounts. While both homodimers and heterodimers are active in DNA synthesis, homogeneous preparations of the heterodimer provide higher stability and processivity than heterogenous mixes of homodimers and heterodimers, as well as improved performance (FIGS. 1 and 2). Unless indicated otherwise, all of RT variants in the following examples were tested as homogeneous preparations of heterodimers.

Example 2: Generation of EIAV RT Mutants

RNase H$^{neg}$ Mutations

Based on homologous mutations that eliminated RNase H activity of commonly studied RTs, i.e. MMLV and HIV-1 RT (Mizuno 2010, Gerard 2002), mutation of the EIAV RT RNase H domain was expected to enhance thermal stability. Thus, RNase H$^{neg}$ variants (EIAV RT V1 and V2; see Table 3 below) of EIAV RT were generated by site directed mutagenesis. When samples of up to 250 ng were tested, neither EIAV RT V1 nor EIAV RT V2 showed detectable RNase H activity (data not shown).

Thumb Domain Mutations

The minor groove binding track (MGBT) in the thumb domain is a highly conserved structural element among retroviral RTs (Beard 1998, Bebenek 1997). Biochemical and molecular modeling studies of HIV-1 RT have revealed that this element is critical for maintaining reading frames, fidelity and processivity by increasing template-primer binding affinity (Beard 1994, Bebenek 1995). Based on sequence alignment of the thumb domain of other lentiviral RTs, five point mutations (M263V/N265K/T267N/M269A/S271Q) within MGBT (EIAV RT V3) were introduced into EIAV RT V1 by site directed mutagenesis.

Random Mutations and Screening on Connection and RNase H Domain.

Key mutations that improve thermostability of RTs have been identified in connection and RNase H domains (Matamoros 2013). To further improve thermostability and processivity, random mutation libraries of connection and RNase H domains were constructed and screened. Based on crystal structures of HIV-1 RT complexed with template/primer and on modeling studies (Huang 1998), a region containing 10 amino acids (355-364) in the connection domain (CD) was chosen for randomization. A CD library was generated by bridging dsDNA with a mixture of 10 ssDNA oligos containing one random amino acid at each position. A random library of RNase H domain variants was generated by error prone PCR. A screening assay of the libraries was performed by measuring RT activity of heat treated (50° C. for 10 min) crude cell lysate at 60° C. The results identified four variants from the CD library and three variants from the RNase H domain library that showed higher RT activity than the parent EIAV RT V3 (data not shown). The best performing CD variant was EIAV RT V4 and the best performing RNase H domain variant was EIAV RT V5. The mutations of EIAV RT V4 and EIAV RT V5 were combined to generate the variant EIAV RT V6.

TABLE 3

EIAV best mode constructs

| Variant | SEQ ID | Mutation | Description of the Effect |
|---|---|---|---|
| EIAV RT WT | SEQ ID NO 2 | none | Heterodimeric wild type enzyme |
| EIAV RT V1 | SEQ ID NO 4 | D443G | Heterodimeric enzyme mutagenized to eliminate RNase H activity |
| EIAV RT V2 | SEQ ID NO 6 | D443G/E476Q | Heterodimeric enzyme mutagenized to eliminate RNase H activity |
| EIAV RT V3 | SEQ ID NO 8 | D443G/M263V/N265K/T267N/M269A/S271Q | Heterodimeric enzyme mutagenized to eliminate RNase H activity and modify the MGBT in thumb domain to increase affinity for template |
| EIAV RT V4 | SEQ ID NO 10 | D443G/M263V/N265K/T267N/M269A/S271Q/I356G/N360A/G362T/W363K | MGBT mutant with additional CD mutations |

TABLE 3-continued

EIAV best mode constructs

| Variant | SEQ ID | Mutation | Description of the Effect |
|---|---|---|---|
| EIAV RT V5 | SEQ ID NO 12 | D443G/M263V/N265K/ T267N/M269A/S271Q/ Q491R/R526H | MGBT mutant with additional RNase H domain mutations |
| EIAV RT V6 | SEQ ID NO 14 | D443G/M263V/N265K/ T267N/M269A/S271Q/ I356G/N360A/G362T/ W363K/Q491R/R526H | MGBT mutant with additional CD and RNase H domain mutations |

Example 3: Assessment of Thermostability and Thermal Activity of RNase H$^{neg}$ Variants Thermostability and thermal activity of the RNase H variants EIAV RT V1 and V2 were evaluated by thermal inactivation assay (FIG. 1) and first strand cDNA synthesis (FIG. 2). In the thermal inactivation assay, RTs were preincubated with a substrate (Oligo (dT)20 primed Poly (A) template) at the 42-60° C. for 10 min. Following preincubation, RT reaction was initiated by adding MgCl$_2$ and the activities were measured by monitoring the relative rates of dT incorporation at 42° C. All the RNase H$^{neg}$ variants (EIAV RT V1 and V2) remained fully active after preincubation at 50° C. whereas heterogeneous EIAV RT WT and homogeneous EIAV RT WT showed 50 and 30% reduced activities, respectively (FIG. 1). Notably, double H$^{neg}$ mutant, EIAV RT V2 retained 80% of its activity even at 55° C. preincubation.

The thermostability of these variants was more stringently evaluated by measuring cDNA synthesis at elevated temperature. First strand cDNA synthesis reactions were performed at 50° C. using a mixture of RNAs ranging in length from 0.5 to 9 kb as template (poly(A)-tailed RNA ladder). Single strand cDNA was resolved by alkaline electrophoresis and visualized by staining with SYBR Gold. As shown in FIG. 2(a), all RNase H$^{neg}$ variants efficiently synthesized full-length cDNAs up to 9 kb, while EIAV RT WT exhibited lower cDNA yield than RNase H$^{neg}$ variants (Lane 1: heterogeneous EIAV RT, Lane 2: homogeneous EIAV RT WT, Lane 3: EIAV RT V1, Lane 4: EIAV RT V2). In contrast, full-length products of any size from heterogeneous EIAV RT WT are near the limit of visual detection, while homogeneous EIAV RT WT yield was slightly lower than the RNase H$^{neg}$ variants.

In a 2-step RT-PCR assay, initial cDNA synthesis reactions were done at 50° C. (FIG. 2(b), upper panel) or 60° C. (FIG. 2(b), lower panel) for 30 min using 10 ng of human total RNA as template. A 2 kb fragment of APC gene was then amplified. All RNase H$^{neg}$ variants generated amplifiable cDNA at both 50° C. and 60° C. whereas homogeneous and heterogeneous EIAV RT both failed to generate cDNA at either 50° C. or 60° C. (FIG. 2(b)). Taken together, these results collectively support the interpretation that abolishing RNase H activity of RT increases its thermostability.

Example 4: Assessment of Thermostability and Thermal Activity of an RNase H$^{neg}$ EIAV RT Variant with Additional Mutations within the MGBT of the Thumb Domain (EIAV RT V3)

Figure 3:
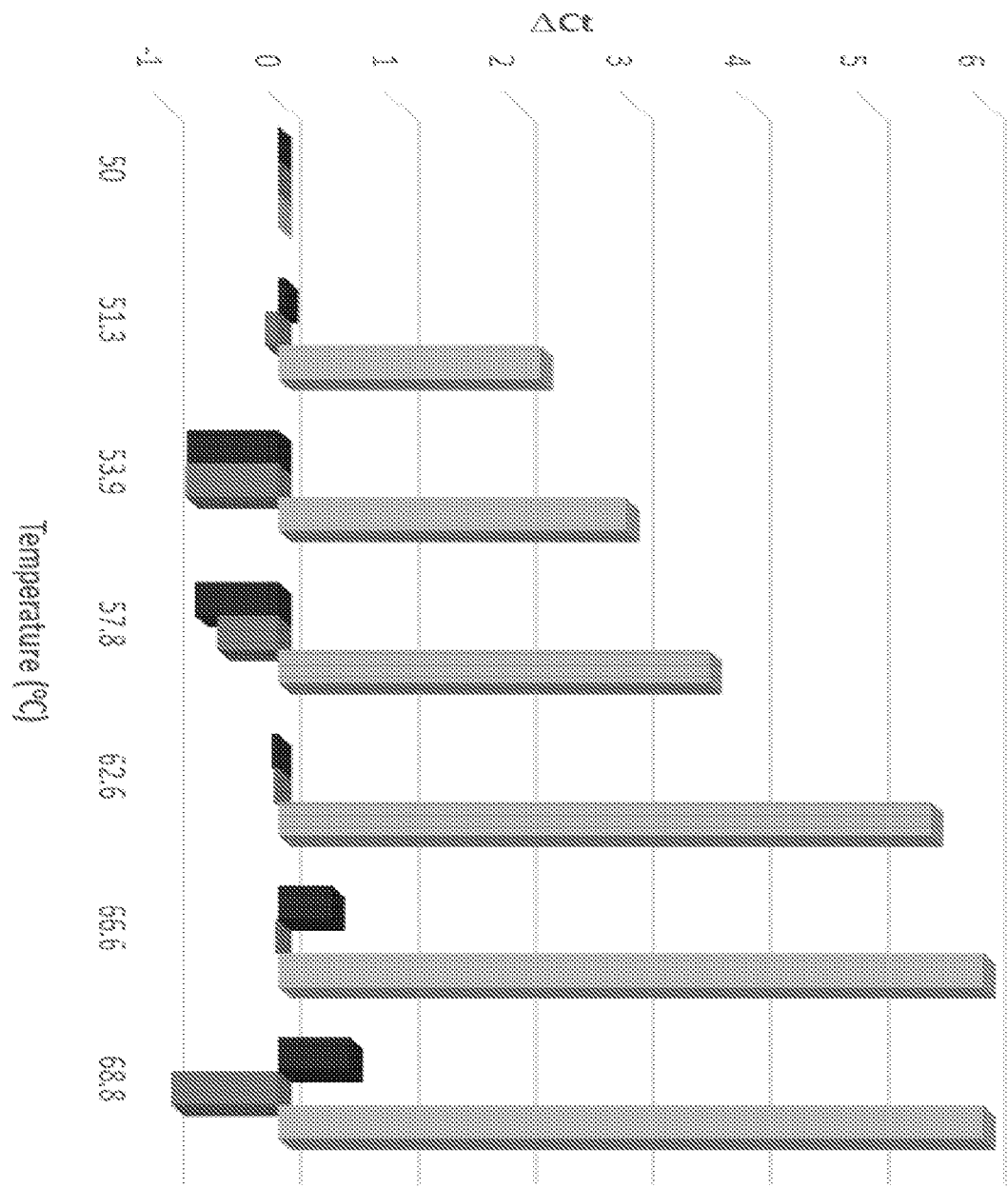
FIG. 3 shows the effect of temperature on cDNA yields in a one step RT-qPCR assay using a state of the art MMLV RT with reduced RNase H activity (EnzScript) and RNase H$^{neg}$ EIAV RT variants according to the invention, wherein EIAV RT V3 additionally comprises point mutations within MGBT.

The effects of the additional mutations on thermostability and thermal activity were evaluated using a FAM probe-based one-step RT-qPCR. First, a region of the ACTB gene was reverse transcribed from human total RNA (2 pg) using EIAV RT V1, EIAV RT V3 or EnzScript RT as indicated, and then amplified and quantified. The results show that both EIAV RT V1 and EIAV RT V3 retain most of their activity close to 70° C. while showing optimal activities at temperature around 55° C. However, reduced activity of EIAV RT V1 becomes noticeable at temperatures higher than 65° C. In contrast, substantial increases of Ct values, denoting reduced cDNA yields, were observed with a typical, widely used comparator EnzScript (a Moloney murine leukemia virus (MMLV) RT with reduced RNase H activity) as temperature increases (FIG. 3).

Figure 4:
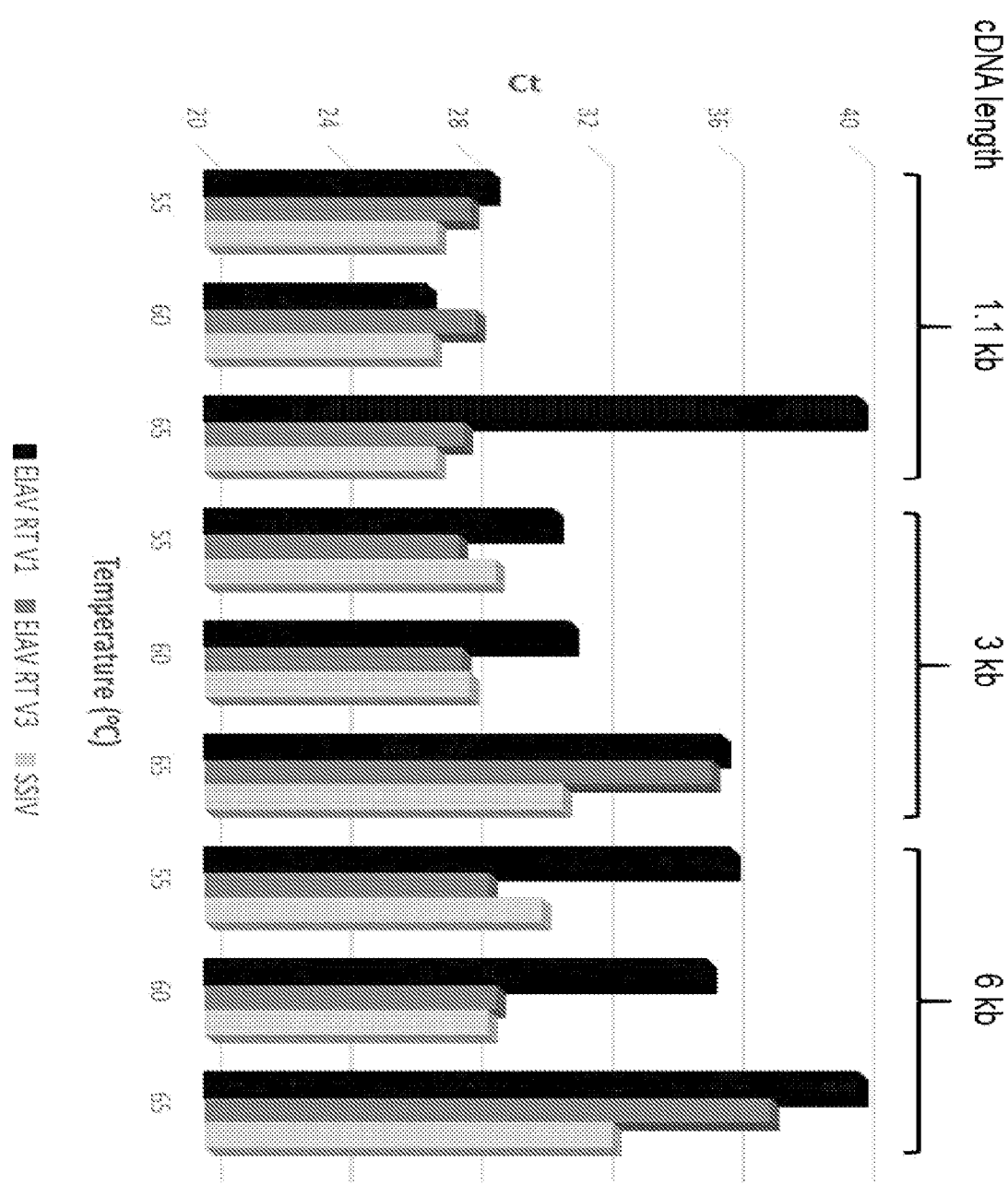
FIG. 4 shows the effect of temperature on the yield of cDNAs of different lengths in a 2-step RT-qPCR assay using a state of the art MMLV RT (SuperScript IV) and EIAV RT variants according to the invention.

Additionally, a 2-step RT-qPCR assay was performed using EIAV RT V1, EIAV RT V3 and SuperScript IV. Using human total RNA (50 ng) and a gene specific primer (MAP4), cDNA was reverse transcribed at the indicated temperatures and cDNAs of different lengths were quantified by qPCR targeting the MAP4 gene. The results demonstrate that EIAV RT V3 generates higher cDNA yield, as shown by lower Ct value, than EIAV RT V1. The difference in yield between these enzymes was dramatically increased at higher temperature or for longer cDNA synthesis indicating improvement of thermostability and processivity of EIAV RT V3 compared with EIAV RT V1 (FIG. 4).

Figure 5:
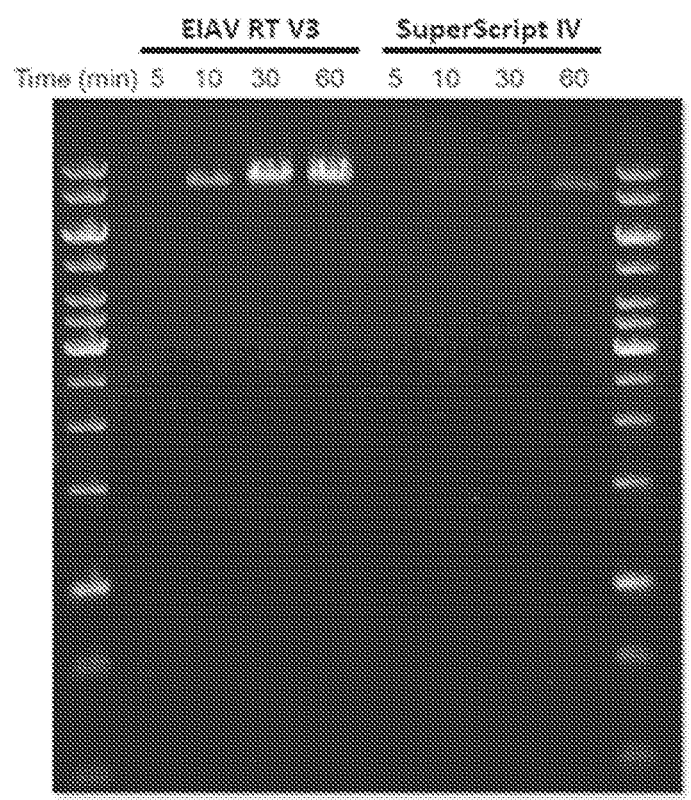
FIG. 5 shows a time course of 9 kb cDNA synthesis at 55° C. by EIAV RT V3 and the state of the art MMLV RT SuperScript IV.

The speed of synthesis and length of product for cDNAs generated by the EIAV RT V3 were compared to SuperScript IV, a widely used commercial RT that is considered state of the art. The reaction was performed using 50 ng of human total RNA as input at 55° C. and Oligo (dT)20 as a primer. The reaction was quenched by heat deactivating RTs at 85° C. for 5 min at indicated times followed by amplification of a 9 kb APC gene. Both enzymes generated amplifiable 9 kb products within 10 min. However, yields were substantially higher with EIAV RT V3 (FIG. 5).

Figure 6:
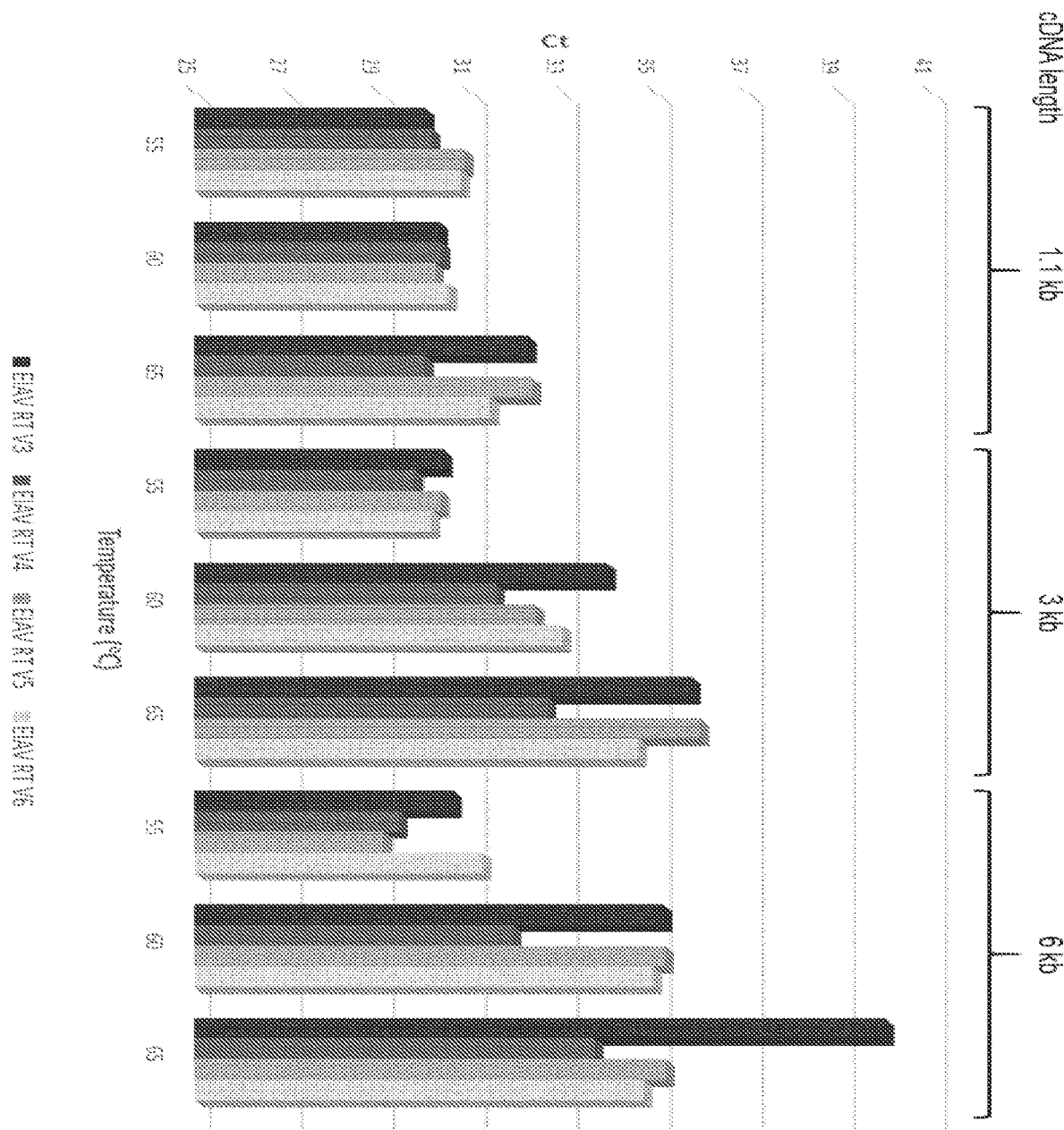
FIG. 6 shows the effect of temperature on cDNA yields in a 2-step RT-qPCR assay using different EIAV RT variants according to the invention.
Figure 7:
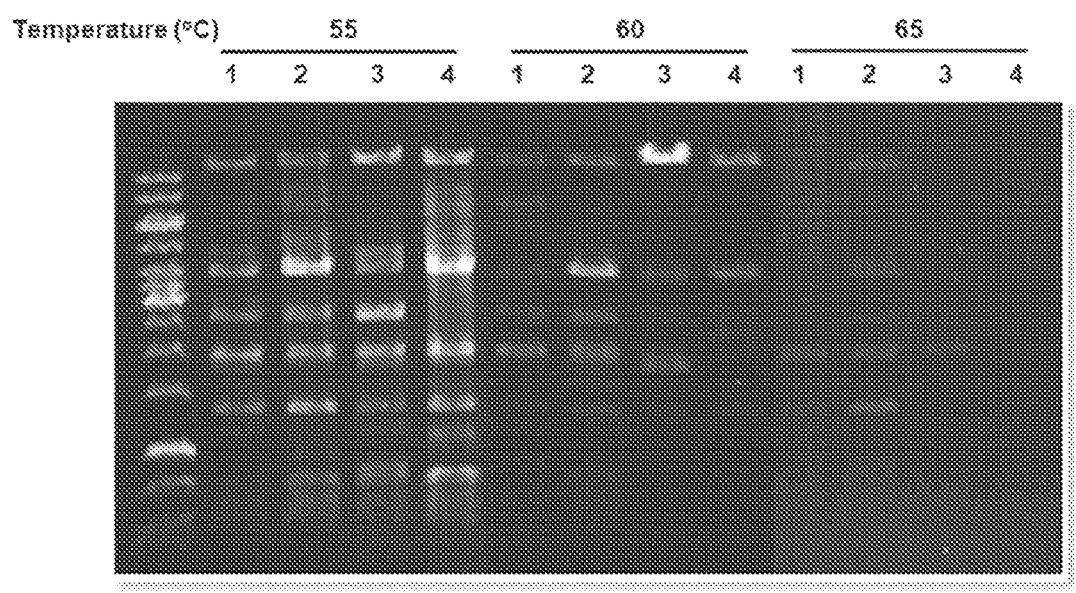
FIG. 7 shows the effect of temperature on cDNA yields in a long-range endpoint PCR assay using different EIAV RT variants according to the invention.

Example 5: Assessment of Thermostability and Thermal Activity of RNase H$^{neg}$/MGBT$^{mut}$ EIAV RT Variants with Additional Mutations within the Connection Domain and/or RNase H Domain The effects of additional mutations within the CD and/or RNase H domain on thermostability and thermal activity were tested in 2 step RT-qPCR (FIG. 6) and a long-range endpoint PCR (FIG. 7).

For the 2 step RT-qPCR, cDNA synthesis using human total RNA (50 ng) and a gene specific primer (MAP4) was performed at the indicated temperatures. Then, cDNA of different lengths were quantified by amplifying MAP4 gene using primer sets designed for the specific regions of the gene. For the long range 2-step RT-PCR (12.3 kb) total rat brain RNA (50 ng) and a gene specific primer for rat dynein were used for the cDNA synthesis at different temperatures (FIG. 7; Lane 1: EIAV RT V3, Lane 2: EIAV RT V4, Lane 3: EIAV RT V5, Lane 4: EIAV RT V6).

Both 2 step RT-qPCR (FIG. 6) and long-range endpoint PCR (FIG. 7) assays at different temperature confirm that all of these variants (EIAV RT V4, EIAV RT V5 and EIAV RT V6) showed increased thermostability and processivity compared with the original EIAV RT V3. One of the constructs, EIAV RT V4, was capable of synthesizing 12.3 kb cDNA at temperatures as high as 65° C. (FIG. 7), and this variant is considered best mode for most applications.

The invention claimed is:

1. A reverse transcriptase comprising two subunits, wherein the two subunits are each encoded by a variant of the polynucleotide sequence of SEQ ID NO:1, wherein the amino acid sequence encoded by the variant is at least 90% identical to the amino acid sequence of SEQ ID NO: 2, wherein the variant comprises mutations in the polynucleotide sequence of SEQ ID NO:1 causing amino acid exchanges relative to the amino acid sequence of SEQ ID NO:2 in the minor groove binding track (MGBT) of the reverse transcriptase's thumb domain, and wherein the mutations in the polynucleotide sequence of SEQ ID NO:1 cause amino acid exchanges within the encoded amino acid sequence at all the amino acid positions that correspond to positions 263, 265, 267, 269, and 271 of SEQ ID NO:2, wherein the amino acid exchanges are M263V, N265K, T267N, M269A, and S271Q.

2. The reverse transcriptase according to claim 1, wherein the variant comprises one or more further mutations in the polynucleotide sequence of SEQ ID NO:1 causing one or more further amino acid exchanges relative to SEQ ID NO: 2 in the reverse transcriptase's connection domain.

3. The reverse transcriptase according to claim 2, wherein the one or more further mutations in the polynucleotide sequence of SEQ ID NO: 1 cause one or more further amino acid exchanges within the encoded amino acid sequence at the amino acid positions that correspond to positions 356, 360, 362, and 363 of SEQ ID NO:2, wherein the amino acid exchanges are I356G/I356D/I356N and/or N360A and/or G362T/G362N and/or W363K/W363N/W363I.

4. The reverse transcriptase according to claim 2, wherein the one or more further mutations in the polynucleotide sequence of SEQ ID NO: 1 cause one or more further amino acid exchanges within the encoded amino acid sequence at the amino acid positions that correspond to positions 356, 360, 362, and 363 of SEQ ID NO:2, wherein the amino acid exchanges are I356G and/or N360A and/or G362T and/or W363K.

5. The reverse transcriptase according to claim 2, wherein the one or more further mutations in the polynucleotide sequence of SEQ ID NO: 1 cause one or more further amino acid exchanges within the encoded amino acid sequence at the amino acid positions that correspond to positions 356, 360, 362, and 363 of SEQ ID NO:2, wherein the amino acid exchanges are I356G, N360A, G362T and W363K.

6. The reverse transcriptase according to claim 1, wherein the variant comprises one or more further mutations in the polynucleotide sequence of SEQ ID NO:1 causing one or more further amino acid exchanges relative to SEQ ID NO:2 in the reverse transcriptase's RNase H domain.

7. The reverse transcriptase according to claim 6, wherein the further mutations in the polynucleotide sequence of SEQ ID NO: 1 cause one or more further amino acid exchanges within the encoded amino acid sequence at the amino acid positions that correspond to positions 443 and 476 of SEQ ID NO:2, wherein the amino acid exchanges are D443G and/or E476Q.

8. The reverse transcriptase according to claim 6, wherein the further mutations in the polynucleotide sequence of SEQ ID NO: 1 cause a further amino acid exchange within the encoded amino acid sequence at the amino acid position that corresponds to position 443 of SEQ ID NO:2, wherein the amino acid exchange is D443G.

9. The reverse transcriptase according to claim 1, wherein the variant comprises a further mutation in the polynucleotide sequence of SEQ ID NO:1 causing a further amino acid exchange relative to SEQ ID NO:2, wherein the further mutation in the polynucleotide sequence of SEQ ID NO:1 causes a further amino acid exchange within the encoded amino acid sequence at the amino acid position that corresponds to position 491 of SEQ ID NO:2, wherein the amino acid exchange is Q491R.

10. The reverse transcriptase according to claim 9, wherein the variant comprises one or more further mutations in the polynucleotide sequence of SEQ ID NO: 1 causing one or more further amino acid exchanges relative to SEQ ID NO:2, wherein the further mutations in the polynucleotide sequence of SEQ ID NO:1 cause one or more further amino acid exchanges within the encoded amino acid sequence at the amino acid positions that correspond to positions 470, 526 and 553 of SEQ ID NO:2, wherein the amino acid exchanges are V470F and/or R526H and/or K533R.

11. The reverse transcriptase according to claim 9, wherein the variant comprises one or more further mutations in the polynucleotide sequence of SEQ ID NO: 1 causing one or more further amino acid exchanges relative to SEQ ID NO:2, wherein the further mutations in the polynucleotide sequence of SEQ ID NO:1 cause one or more further amino acid exchanges within the encoded amino acid sequence at the amino acid positions that correspond to positions 526 and 553 of SEQ ID NO:2, wherein the amino acid exchanges are R526H and/or K553R.

12. The reverse transcriptase according to claim 9, wherein the variant comprises one or more further mutations in the polynucleotide sequence of SEQ ID NO: 1 causing one or more further amino acid exchanges relative to SEQ ID NO:2, wherein the further mutations in the polynucleotide sequence of SEQ ID NO:1 cause a further amino acid exchange within the encoded amino acid sequence at the amino acid position that corresponds to position 526 of SEQ ID NO:2, wherein the amino acid exchange is R526H.

13. The reverse transcriptase according to claim 1, wherein the mutations in the polynucleotide sequence of SEQ ID NO: 1 cause amino acid exchanges within the encoded amino acid sequence at all the amino acid positions that correspond to positions 263, 265, 267, 269, 271, 356, 360, 362, 363 and 443 of SEQ ID NO:2, wherein the amino acid exchanges are M263V, N265K, T267N, M269A, S271Q, I356G, N360A, G362T, W363K and D443G.

14. The reverse transcriptase according to claim 1, wherein a first subunit of the two subunits comprises the complete amino acid sequence encoded by the variant and wherein a second subunit of the two subunits comprises a proteolytic fragment of the complete amino acid sequence encoded by the variant.

15. A kit comprising:
a) the reverse transcriptase of claim 1; and
b) a buffer.

16. A polynucleotide encoding an reverse transcriptase according to claim 1.

17. A vector comprising the polynucleotide according to claim 16.

18. A transformed host cell comprising the vector according to claim 17.

19. A reverse transcriptase obtained by expression of the polynucleotide according to claim 16 in a host cell.

20. The reverse transcriptase according to claim 19, wherein the host cell is E. coli.

21. A reverse transcriptase obtained by expression of the vector according to claim 17 in a host cell.

22. The reverse transcriptase according to claim 21, wherein the host cell is E. coli.

23. A method for amplifying template nucleic acids comprising contacting the template nucleic acids with an reverse transcriptase according to claim 1.

24. The method according to claim 23, wherein the method is reverse transcription (RT) PCR.

* * * * *

UNITED STATES PATENT AND TRADEMARK OFFICE
CERTIFICATE OF CORRECTION

| | | |
|---|---|---|
| PATENT NO. | : 12,398,381 B2 | Page 1 of 1 |
| APPLICATION NO. | : 17/761053 | |
| DATED | : August 26, 2025 | |
| INVENTOR(S) | : Suhman Chung et al. | |

It is certified that error appears in the above-identified patent and that said Letters Patent is hereby corrected as shown below:

In the Claims

In Column 70, Line 58, delete "1356G/1356D/1356N" and insert --I356G/I356D/I356N--

In Column 71, Line 7, delete "1356G," and insert --I356G,--

Signed and Sealed this
Twenty-fifth Day of November, 2025

John A. Squires
*Director of the United States Patent and Trademark Office*

SEQUENCE LISTING

<160> NUMBER OF SEQ ID NOS: 19

<210> SEQ ID NO 1
<211> LENGTH: 1674
<212> TYPE: DNA
<213> ORGANISM: Artificial Sequence
<220> FEATURE:
<221> NAME/KEY: source
<222> LOCATION: 1..1674
<223> OTHER INFORMATION: /mol_type="unassigned DNA"
      /note="Synthetic gene"
      /organism="Artificial Sequence"

<400> SEQUENCE: 1

```
atggcacagc tgagcaaaga aatcaaattt cgcaaaatcg aactgaaaga aggcaccatg      60
ggtccgaaaa ttccgcagtg gcctctgacc aaagaaaaac tggaaggtgc aaaagaaatt     120
gttcagcgtc tgctgagcga aggtaaaatt agcgaagcaa gcgataataa cccgtataac     180
agcccgattt tcgtgatcaa aaaacgtagc ggtaaatggc gtctgctgca ggatctgcgt     240
gaactgaata aaccgttca ggttggcacc gaaattagcc gtggtctgcc gcatccgggt     300
ggtctgatta aatgtaaaca catgaccgtt ctggatattg cgacgcata ttttaccatt     360
ccgctggatc cggaatttcg tccgtatacc gcatttacaa ttccgagcat taatcatcaa     420
gaaccggata acgttatgt gtggaattgc ctgccgcagg ttttgttct gagcccgtat     480
atctatcaga aaacgctgca agaaattctg cagccatttc gtgaacgtta tccggaagtt     540
cagctgtatc agtatatgga tgacctgttt gtgggtagca atggtagcaa aaaacagcac     600
aaagaactga tcattgaact gcgtgcaatt ctgctggaaa aaggttttga acaccggat     660
gataaactgc aagaagttcc gccttatagc tggctgggtt atcagctgtg tccggaaaat     720
tggaaagttc agaaaatgca gctggatatg gttaaaaatc gcaccctgaa tgatgtgcag     780
aaactgatgg gcaatattac ctggatgagc agcggtgttc cgggtctgac cgttaaacat     840
attgcagcaa ccaccaaagg ttgtctggaa ctgaatcaga agttatctg gaccgaagaa     900
gcacaaaaag aactggaaga aaacaacgag aaaatcaaaa atgcacaggg cctgcagtat     960
tataacccgg aagaagaaat gctttgcgaa gtggaaatca ccaaaaacta tgaagccacc    1020
tatgtgatta acagagcca gggtattctg tgggcaggca aaaaaatcat gaaagccaat    1080
aaaggttgga gcaccgtgaa aaatctgatg ctgctgctgc aacatgtggc aaccgaaagc    1140
attacccgtg ttggtaaatg tccgacctt aaagttccgt ttaccaaaga acaggtgatg    1200
tgggaaatgc agaaaggttg gtattatagt tggctgccgg aaattgttta cccatcag    1260
gttgttcatg atgactggcg tatgaaactg gttgaagaac cgaccagcgg tattaccatt    1320
tataccgatg gtggtaaaca gaatggtgaa ggtattgcag cctatgttac cagcaatggt    1380
cgtaccaaac agaaacgtct gggtccggtt acacatcagg tggcagaacg tatggcaatt    1440
cagatggcac tggaagatac ccgtgataaa caggttaata ttgtgaccga tagctattat    1500
tgttggaaaa acattaccga aggtctgggt ctggaaggtc gcagagccc gtggtggccg    1560
attattcaga atattcgcga aaaagaaatc gtgtactttg catgggttcc aggtcataaa    1620
ggtatttgtg gtaatcagct ggcagatgaa gcagccaaaa tcaaagaaga gatc         1674
```

<210> SEQ ID NO 2
<211> LENGTH: 558
<212> TYPE: PRT
<213> ORGANISM: Artificial Sequence
<220> FEATURE:
<223> OTHER INFORMATION: Expression from a synthetic gene

<400> SEQUENCE: 2

Met Ala Gln Leu Ser Lys Glu Ile Lys Phe Arg Lys Ile Glu Leu Lys
1               5                   10                  15

Glu Gly Thr Met Gly Pro Lys Ile Pro Gln Trp Pro Leu Thr Lys Glu
            20                  25                  30

Lys Leu Glu Gly Ala Lys Glu Ile Val Gln Arg Leu Leu Ser Glu Gly
                35                  40                  45

Lys Ile Ser Glu Ala Ser Asp Asn Asn Pro Tyr Asn Ser Pro Ile Phe
        50                  55                  60

Val Ile Lys Lys Arg Ser Gly Lys Trp Arg Leu Leu Gln Asp Leu Arg
65                  70                  75                  80

Glu Leu Asn Lys Thr Val Gln Val Gly Thr Glu Ile Ser Arg Gly Leu
                85                  90                  95

Pro His Pro Gly Gly Leu Ile Lys Cys Lys His Met Thr Val Leu Asp
            100                 105                 110

Ile Gly Asp Ala Tyr Phe Thr Ile Pro Leu Asp Pro Glu Phe Arg Pro
                115                 120                 125

Tyr Thr Ala Phe Thr Ile Pro Ser Ile Asn His Gln Glu Pro Asp Lys
        130                 135                 140

Arg Tyr Val Trp Asn Cys Leu Pro Gln Gly Phe Val Leu Ser Pro Tyr
145                 150                 155                 160

Ile Tyr Gln Lys Thr Leu Gln Glu Ile Leu Gln Pro Phe Arg Glu Arg
                165                 170                 175

Tyr Pro Glu Val Gln Leu Tyr Gln Tyr Met Asp Asp Leu Phe Val Gly
            180                 185                 190

Ser Asn Gly Ser Lys Lys Gln His Lys Glu Leu Ile Ile Glu Leu Arg
                195                 200                 205

Ala Ile Leu Leu Glu Lys Gly Phe Glu Thr Pro Asp Asp Lys Leu Gln
        210                 215                 220

Glu Val Pro Pro Tyr Ser Trp Leu Gly Tyr Gln Leu Cys Pro Glu Asn
225                 230                 235                 240

Trp Lys Val Gln Lys Met Gln Leu Asp Met Val Lys Asn Pro Thr Leu
                245                 250                 255

Asn Asp Val Gln Lys Leu Met Gly Asn Ile Thr Trp Met Ser Ser Gly
            260                 265                 270

Val Pro Gly Leu Thr Val Lys His Ile Ala Ala Thr Thr Lys Gly Cys
        275                 280                 285

Leu Glu Leu Asn Gln Lys Val Ile Trp Thr Glu Glu Ala Gln Lys Glu
        290                 295                 300

Leu Glu Glu Asn Asn Glu Lys Ile Lys Asn Ala Gln Gly Leu Gln Tyr
305                 310                 315                 320

Tyr Asn Pro Glu Glu Glu Met Leu Cys Glu Val Glu Ile Thr Lys Asn
                325                 330                 335

Tyr Glu Ala Thr Tyr Val Ile Lys Gln Ser Gly Ile Leu Trp Ala
            340                 345                 350

Gly Lys Lys Ile Met Lys Ala Asn Lys Gly Trp Ser Thr Val Lys Asn
        355                 360                 365

Leu Met Leu Leu Leu Gln His Val Ala Thr Glu Ser Ile Thr Arg Val
            370                 375                 380

Gly Lys Cys Pro Thr Phe Lys Val Pro Phe Thr Lys Glu Gln Val Met
385                 390                 395                 400

Trp Glu Met Gln Lys Gly Trp Tyr Tyr Ser Trp Leu Pro Glu Ile Val

```
                405                 410                 415
Tyr Thr His Gln Val His Asp Asp Trp Arg Met Lys Leu Val Glu
            420                 425                 430

Glu Pro Thr Ser Gly Ile Thr Ile Tyr Thr Asp Gly Gly Lys Gln Asn
            435                 440                 445

Gly Glu Gly Ile Ala Ala Tyr Val Thr Ser Asn Gly Arg Thr Lys Gln
            450                 455                 460

Lys Arg Leu Gly Pro Val Thr His Gln Val Ala Glu Arg Met Ala Ile
465                 470                 475                 480

Gln Met Ala Leu Glu Asp Thr Arg Asp Lys Gln Val Asn Ile Val Thr
                485                 490                 495

Asp Ser Tyr Tyr Cys Trp Lys Asn Ile Thr Glu Gly Leu Gly Leu Glu
                500                 505                 510

Gly Pro Gln Ser Pro Trp Trp Pro Ile Ile Gln Asn Ile Arg Glu Lys
                515                 520                 525

Glu Ile Val Tyr Phe Ala Trp Val Pro Gly His Lys Gly Ile Cys Gly
                530                 535                 540

Asn Gln Leu Ala Asp Glu Ala Ala Lys Ile Lys Glu Glu Ile
545                 550                 555

<210> SEQ ID NO 3
<211> LENGTH: 1674
<212> TYPE: DNA
<213> ORGANISM: Artificial Sequence
<220> FEATURE:
<221> NAME/KEY: source
<222> LOCATION: 1..1674
<223> OTHER INFORMATION: /mol_type="unassigned DNA"
     /note="Synthetic gene"
     /organism="Artificial Sequence"

<400> SEQUENCE: 3
atggcacagc tgagcaaaga aatcaaattt cgcaaaatcg aactgaaaga aggcaccatg      60
ggtccgaaaa ttccgcagtg gcctctgacc aaagaaaaac tggaaggtgc aaaagaaatt     120
gttcagcgtc tgctgagcga aggtaaaatt agcgaagcaa gcgataataa cccgtataac     180
agcccgattt tcgtgatcaa aaaacgtagc ggtaaatggc gtctgctgca ggatctgcgt     240
gaactgaata aaccgttcag gttggcacc gaaattagcc gtggtctgcc gcatccgggt     300
ggtctgatta aatgtaaaca catgaccgtt ctggatattg cgacgcata ttttaccatt     360 ccgctggatc cggaatttcg tccgtatacc gcatttacaa ttccgagcat taatcatcaa     420
gaaccggata acgttatgt gtggaattgc ctgccgcagg ttttgttct gagcccgtat     480 atctatcaga aaacgctgca agaaattctg cagccatttc gtgaacgtta ccggaagtt     540 cagctgtatc agtatatgga tgacctgttt gtgggtagca atggtagcaa aaaacagcac     600
aaagaactga tcattgaact gcgtgcaatt ctgctggaaa aaggtttga acaccggat     660 gataaactgc aagaagttcc gccttatagc tggctgggtt atcagctgtg tccggaaaat     720
tggaaagttc agaaaatgca gctggatatg gttaaaaatc gaccctgaa tgatgtgcag     780 aaactgatgg gcaatattac ctggatgagc agcggtgttc gggtctgac cgttaaacat     840 attgcagcaa ccaccaaagg ttgtctggaa ctgaatcaga agttatctg gaccgaagaa     900 gcacaaaaag aactggaaga aacaacgag aaaatcaaaa atgcacaggg cctgcagtat     960
tataacccgg aagaagaaat gctttgcgaa gtggaaatca ccaaaaacta tgaagccacc    1020
tatgtgatta acagagcca gggtattctg tgggcaggca aaaaaatcat gaaagccaat    1080
```

-continued

| | |
|---|---|
| aaaggttgga gcaccgtgaa aaatctgatg ctgctgctgc aacatgtggc aaccgaaagc | 1140 |
| attacccgtg ttggtaaatg tccgaccttt aaagttccgt ttaccaaaga acaggtgatg | 1200 |
| tgggaaatgc agaaaggttg gtattatagt tggctgccgg aaattgttta tacccatcag | 1260 |
| gttgttcatg atgactggcg tatgaaactg gttgaagaac cgaccagcgg tattaccatt | 1320 |
| tataccggtg gtggtaaaca gaatggtgaa ggtattgcag cctatgttac agcaatggt | 1380 |
| cgtaccaaac agaaacgtct gggtccggtt acacatcagg tggcagaacg tatggcaatt | 1440 |
| cagatggcac tggaagatac ccgtgataaa caggttaata ttgtgaccga tagctattat | 1500 |
| tgttggaaaa acattaccga aggtctgggt ctggaaggtc cgcagagccc gtggtggccg | 1560 |
| attattcaga atattcgcga aaagaaatc gtgtactttg catgggttcc aggtcataaa | 1620 |
| ggtatttgtg gtaatcagct ggcagatgaa gcagccaaaa tcaaagaaga gatc | 1674 |

<210> SEQ ID NO 4
<211> LENGTH: 558
<212> TYPE: PRT
<213> ORGANISM: Artificial Sequence
<220> FEATURE:
<223> OTHER INFORMATION: Expression from a synthetic gene

<400> SEQUENCE: 4

```
Met Ala Gln Leu Ser Lys Glu Ile Lys Phe Arg Lys Ile Glu Leu Lys
1               5                   10                  15

Glu Gly Thr Met Gly Pro Lys Ile Pro Gln Trp Pro Leu Thr Lys Glu
            20                  25                  30

Lys Leu Glu Gly Ala Lys Glu Ile Val Gln Arg Leu Leu Ser Glu Gly
        35                  40                  45

Lys Ile Ser Glu Ala Ser Asp Asn Asn Pro Tyr Asn Ser Pro Ile Phe
    50                  55                  60

Val Ile Lys Lys Arg Ser Gly Lys Trp Arg Leu Leu Gln Asp Leu Arg
65                  70                  75                  80

Glu Leu Asn Lys Thr Val Gln Val Gly Thr Glu Ile Ser Arg Gly Leu
                85                  90                  95

Pro His Pro Gly Gly Leu Ile Lys Cys Lys His Met Thr Val Leu Asp
            100                 105                 110

Ile Gly Asp Ala Tyr Phe Thr Ile Pro Leu Asp Pro Glu Phe Arg Pro
        115                 120                 125

Tyr Thr Ala Phe Thr Ile Pro Ser Ile Asn His Gln Glu Pro Asp Lys
    130                 135                 140

Arg Tyr Val Trp Asn Cys Leu Pro Gln Gly Phe Val Leu Ser Pro Tyr
145                 150                 155                 160

Ile Tyr Gln Lys Thr Leu Gln Glu Ile Leu Gln Pro Phe Arg Glu Arg
                165                 170                 175

Tyr Pro Glu Val Gln Leu Tyr Gln Tyr Met Asp Asp Leu Phe Val Gly
            180                 185                 190

Ser Asn Gly Ser Lys Lys Gln His Lys Glu Leu Ile Ile Glu Leu Arg
        195                 200                 205

Ala Ile Leu Leu Glu Lys Gly Phe Glu Thr Pro Asp Asp Lys Leu Gln
    210                 215                 220

Glu Val Pro Pro Tyr Ser Trp Leu Gly Tyr Gln Leu Cys Pro Glu Asn
225                 230                 235                 240

Trp Lys Val Gln Lys Met Gln Leu Asp Met Val Lys Asn Pro Thr Leu
                245                 250                 255

Asn Asp Val Gln Lys Leu Met Gly Asn Ile Thr Trp Met Ser Ser Gly
```

```
                260               265               270
Val Pro Gly Leu Thr Val Lys His Ile Ala Thr Thr Lys Gly Cys
            275               280               285

Leu Glu Leu Asn Gln Lys Val Ile Trp Thr Glu Ala Gln Lys Glu
        290               295               300

Leu Glu Glu Asn Asn Glu Lys Ile Lys Asn Ala Gln Gly Leu Gln Tyr
305               310               315               320

Tyr Asn Pro Glu Glu Glu Met Leu Cys Glu Val Glu Ile Thr Lys Asn
                325               330               335

Tyr Glu Ala Thr Tyr Val Ile Lys Gln Ser Gln Gly Ile Leu Trp Ala
            340               345               350

Gly Lys Lys Ile Met Lys Ala Asn Lys Gly Trp Ser Thr Val Lys Asn
            355               360               365

Leu Met Leu Leu Leu Gln His Val Ala Thr Glu Ser Ile Thr Arg Val
        370               375               380

Gly Lys Cys Pro Thr Phe Lys Val Pro Phe Thr Lys Glu Gln Val Met
385               390               395               400

Trp Glu Met Gln Lys Gly Trp Tyr Tyr Ser Trp Leu Pro Glu Ile Val
                405               410               415

Tyr Thr His Gln Val Val His Asp Asp Trp Arg Met Lys Leu Val Glu
            420               425               430

Glu Pro Thr Ser Gly Ile Thr Ile Tyr Thr Gly Gly Lys Gln Asn
            435               440               445

Gly Glu Gly Ile Ala Ala Tyr Val Thr Ser Asn Gly Arg Thr Lys Gln
        450               455               460

Lys Arg Leu Gly Pro Val Thr His Gln Val Ala Glu Arg Met Ala Ile
465               470               475               480

Gln Met Ala Leu Glu Asp Thr Arg Asp Lys Gln Val Asn Ile Val Thr
                485               490               495

Asp Ser Tyr Tyr Cys Trp Lys Asn Ile Thr Glu Gly Leu Gly Leu Glu
            500               505               510

Gly Pro Gln Ser Pro Trp Trp Pro Ile Ile Gln Asn Ile Arg Glu Lys
        515               520               525

Glu Ile Val Tyr Phe Ala Trp Val Pro Gly His Lys Gly Ile Cys Gly
    530               535               540

Asn Gln Leu Ala Asp Glu Ala Ala Lys Ile Lys Glu Glu Ile
545               550               555

<210> SEQ ID NO 5
<211> LENGTH: 1674
<212> TYPE: DNA
<213> ORGANISM: Artificial Sequence
<220> FEATURE:
<221> NAME/KEY: source
<222> LOCATION: 1..1674
<223> OTHER INFORMATION: /mol_type="unassigned DNA"
      /note="Synthetic gene"
      /organism="Artificial Sequence"

<400> SEQUENCE: 5
atggcacagc tgagcaaaga aatcaaattt cgcaaaatcg aactgaaaga aggcaccatg      60
ggtccgaaaa ttccgcagtg gcctctgacc aaagaaaaac tggaaggtgc aaaagaaatt     120
gttcagcgtc tgctgagcga aggtaaaatt agcgaagcaa gcgataataa cccgtataac     180
agcccgattt tcgtgatcaa aaaacgtagc ggtaaatggc gtctgctgca ggatctgcgt     240
gaactgaata aaaccgttca ggttggcacc gaaattagcc gtggtctgcc gcatccgggt     300
```

```
ggtctgatta aatgtaaaca catgaccgtt ctggatattg cgacgcata ttttaccatt      360 ccgctggatc cggaatttcg tccgtatacc gcatttacaa ttccgagcat taatcatcaa      420
gaaccggata acgttatgt gtggaattgc ctgccgcagg ttttgttct gagcccgtat       480 atctatcaga aaacgctgca agaaattctg cagccatttc gtgaacgtta tccggaagtt      540
cagctgtatc agtatatgga tgacctgttt gtgggtagca atggtagcaa aaaacagcac      600
aaagaactga tcattgaact gcgtgcaatt ctgctggaaa aaggttttga acaccggat       660 gataaactgc aagaagttcc gccttatagc tggctgggtt atcagctgtg tccggaaaat      720
tggaaagttc agaaaatgca gctggatatg gttaaaaatc cgaccctgaa tgatgtgcag      780
aaactgatgg gcaatattac ctggatgagc agcggtgttc cgggtctgac cgttaaacat      840
attgcagcaa ccaccaaagg ttgtctggaa ctgaatcaga aagttatctg gaccgaagaa      900
gcacaaaaag aactggaaga aaacaacgag aaaatcaaaa atgcacaggg cctgcagtat      960 tataaccccgg aagaagaaat gctttgcgaa gtggaaatca ccaaaaacta tgaagccacc     1020
tatgtgatta acagagcca gggtattctg tgggcaggca aaaaaatcat gaaagccaat      1080
aaaggttgga gcaccgtgaa aaatctgatg ctgctgctgc aacatgtggc aaccgaaagc     1140
attacccgtg ttggtaaatg tccgaccttt aaagttccgt taccaaaga acaggtgatg     1200 tgggaaatgc agaaaggttg gtattatagt tggctgccgg aaattgttta tacccatcag     1260
gttgttcatg atgactggcg tatgaaactg gttgaagaac cgaccagcgg tattaccatt     1320
tataccggtg gtggtaaaca gaatggtgaa ggtattgcag cctatgttac cagcaatggt     1380
cgtaccaaac agaaacgtct gggtccggtt acacatcagg tggcacaacg tatggcaatt     1440
cagatggcac tggaagatac ccgtgataaa caggttaata ttgtgaccga tagctattat     1500
tgttggaaaa acattaccga aggtctgggt ctggaaggtc cgcagagccc gtggtggccg     1560
attattcaga atattcgcga aaagaaatc gtgtactttg catgggttcc aggtcataaa     1620
ggtatttgtg gtaatcagct ggcagatgaa gcagccaaaa tcaaagaaga gatc           1674
```

<210> SEQ ID NO 6
<211> LENGTH: 558
<212> TYPE: PRT
<213> ORGANISM: Artificial Sequence
<220> FEATURE:
<223> OTHER INFORMATION: Expression from a synthetic gene

<400> SEQUENCE: 6

```
Met Ala Gln Leu Ser Lys Glu Ile Lys Phe Arg Lys Ile Glu Leu Lys
1               5                   10                  15

Glu Gly Thr Met Gly Pro Lys Ile Pro Gln Trp Pro Leu Thr Lys Glu
            20                  25                  30

Lys Leu Glu Gly Ala Lys Glu Ile Val Gln Arg Leu Leu Ser Glu Gly
        35                  40                  45

Lys Ile Ser Glu Ala Ser Asp Asn Asn Pro Tyr Asn Ser Pro Ile Phe
    50                  55                  60

Val Ile Lys Lys Arg Ser Gly Lys Trp Arg Leu Leu Gln Asp Leu Arg
65                  70                  75                  80

Glu Leu Asn Lys Thr Val Gln Val Gly Thr Glu Ile Ser Arg Gly Leu
                85                  90                  95

Pro His Pro Gly Gly Leu Ile Lys Cys Lys His Met Thr Val Leu Asp
            100                 105                 110

Ile Gly Asp Ala Tyr Phe Thr Ile Pro Leu Asp Pro Glu Phe Arg Pro
```

```
            115                 120                 125
Tyr Thr Ala Phe Thr Ile Pro Ser Ile Asn His Gln Glu Pro Asp Lys
        130                 135                 140

Arg Tyr Val Trp Asn Cys Leu Pro Gln Gly Phe Val Leu Ser Pro Tyr
145                 150                 155                 160

Ile Tyr Gln Lys Thr Leu Gln Glu Ile Leu Gln Pro Phe Arg Glu Arg
                165                 170                 175

Tyr Pro Glu Val Gln Leu Tyr Gln Tyr Met Asp Asp Leu Phe Val Gly
            180                 185                 190

Ser Asn Gly Ser Lys Lys Gln His Lys Glu Leu Ile Ile Glu Leu Arg
        195                 200                 205

Ala Ile Leu Leu Glu Lys Gly Phe Glu Thr Pro Asp Asp Lys Leu Gln
210                 215                 220

Glu Val Pro Pro Tyr Ser Trp Leu Gly Tyr Gln Leu Cys Pro Glu Asn
225                 230                 235                 240

Trp Lys Val Gln Lys Met Gln Leu Asp Met Val Lys Asn Pro Thr Leu
                245                 250                 255

Asn Asp Val Gln Lys Leu Met Gly Asn Ile Thr Trp Met Ser Ser Gly
            260                 265                 270

Val Pro Gly Leu Thr Val Lys His Ile Ala Ala Thr Thr Lys Gly Cys
        275                 280                 285

Leu Glu Leu Asn Gln Lys Val Ile Trp Thr Glu Glu Ala Gln Lys Glu
290                 295                 300

Leu Glu Glu Asn Asn Glu Lys Ile Lys Asn Ala Gln Gly Leu Gln Tyr
305                 310                 315                 320

Tyr Asn Pro Glu Glu Glu Met Leu Cys Glu Val Glu Ile Thr Lys Asn
                325                 330                 335

Tyr Glu Ala Thr Tyr Val Ile Lys Gln Ser Gln Gly Ile Leu Trp Ala
            340                 345                 350

Gly Lys Lys Ile Met Lys Ala Asn Lys Gly Trp Ser Thr Val Lys Asn
        355                 360                 365

Leu Met Leu Leu Leu Gln His Val Ala Thr Glu Ser Ile Thr Arg Val
370                 375                 380

Gly Lys Cys Pro Thr Phe Lys Val Pro Phe Thr Lys Glu Gln Val Met
385                 390                 395                 400

Trp Glu Met Gln Lys Gly Trp Tyr Tyr Ser Trp Leu Pro Glu Ile Val
                405                 410                 415

Tyr Thr His Gln Val Val His Asp Asp Trp Arg Met Lys Leu Val Glu
            420                 425                 430

Glu Pro Thr Ser Gly Ile Thr Ile Tyr Thr Gly Gly Lys Gln Asn
        435                 440                 445

Gly Glu Gly Ile Ala Ala Tyr Val Thr Ser Asn Gly Arg Thr Lys Gln
        450                 455                 460

Lys Arg Leu Gly Pro Val Thr His Gln Val Ala Gln Arg Met Ala Ile
465                 470                 475                 480

Gln Met Ala Leu Glu Asp Thr Arg Asp Lys Gln Val Asn Ile Val Thr
                485                 490                 495

Asp Ser Tyr Tyr Cys Trp Lys Asn Ile Thr Glu Gly Leu Gly Leu Glu
            500                 505                 510

Gly Pro Gln Ser Pro Trp Trp Pro Ile Ile Gln Asn Ile Arg Glu Lys
        515                 520                 525

Glu Ile Val Tyr Phe Ala Trp Val Pro Gly His Lys Gly Ile Cys Gly
530                 535                 540
```

Asn Gln Leu Ala Asp Glu Ala Ala Lys Ile Lys Glu Glu Ile
545                 550                 555

<210> SEQ ID NO 7
<211> LENGTH: 1674
<212> TYPE: DNA
<213> ORGANISM: Artificial Sequence
<220> FEATURE:
<221> NAME/KEY: source
<222> LOCATION: 1..1674
<223> OTHER INFORMATION: /mol_type="unassigned DNA"
      /note="Synthetic gene"
      /organism="Artificial Sequence"

<400> SEQUENCE: 7

```
atggcacagc tgagcaaaga aatcaaattt cgcaaaatcg aactgaaaga aggcaccatg      60
ggtccgaaaa ttccgcagtg gcctctgacc aaagaaaaac tggaaggtgc aaaagaaatt     120
gttcagcgtc tgctgagcga aggtaaaatt agcgaagcaa gcgataataa cccgtataac     180
agcccgattt tcgtgatcaa aaaacgtagc ggtaaatggc gtctgctgca ggatctgcgt     240
gaactgaata aaccgttcag gttggcacc gaaattagcc gtggtctgcc gcatccgggt      300
ggtctgatta atgtaaaca catgaccgtt ctggatattg cgacgcata ttttaccatt       360
ccgctggatc cggaatttcg tccgtatacc gcatttacaa ttccgagcat taatcatcaa     420
gaaccggata acgttatgt gtggaattgc ctgccgcagg ttttgttct gagcccgtat       480
atctatcaga aaacgctgca agaaattctg cagccatttc gtgaacgtta tccggaagtt    540
cagctgtatc agtatatgga tgacctgttt gtgggtagca atggtagcaa aaaacagcac    600
aaagaactga tcattgaact gcgtgcaatt ctgctggaaa aaggttttga acaccggat     660
gataaactgc aagaagttcc gccttatagc tggctgggtt atcagctgtg tccggaaaat    720
tggaaagttc agaaaatgca gctggatatg gttaaaaatc cgaccctgaa tgatgtgcag    780
aaactggtgg gcaaaattaa ttgggctagc cagggtgttc cgggtctgac cgttaaacat    840
attgcagcaa ccaccaaagg ttgtctggaa ctgaatcaga agttatctg gaccgaagaa     900
gcacaaaaag aactggaaga aacaacgag aaaatcaaaa atgcacaggg cctgcagtat     960
tataacccgg aagaagaaat gctttgcgaa gtggaaatca ccaaaaacta tgaagccacc   1020
tatgtgatta acagagcca gggtattctg tgggcaggca aaaaaatcat gaaagccaat    1080
aaaggttgga gcaccgtgaa aaatctgatg ctgctgctgc aacatgtggc aaccgaaagc   1140
attacccgtg ttggtaaatg tccgaccttt aaagttccgt ttaccaaaga acaggtgatg   1200
tgggaaatgc agaaaggttg gtattatagt tggctgccgg aaattgttta tacccatcag   1260
gttgttcatg atgactggcg tatgaaactg gttaagaac cgaccagcgg tattaccatt   1320
tataccggtg gtggtaaaca gaatggtgaa ggtattgcag cctatgttac cagcaatggt   1380
cgtaccaaac agaaacgtct gggtccggtt acacatcagg tggcagaacg tatggcaatt   1440
cagatggcac tggaagatac ccgtgataaa caggttaata ttgtgaccga tagctattat   1500
tgttggaaaa acattaccga aggtctgggt ctggaaggtc gcagagccc gtggtggccg    1560
attattcaga atattcgcga aaagaaaatc gtgtactttg catgggttcc aggtcataaa   1620
ggtatttgtg gtaatcagct ggcagatgaa gcagccaaaa tcaaagaaga gatc          1674
```

<210> SEQ ID NO 8
<211> LENGTH: 558
<212> TYPE: PRT
<213> ORGANISM: Artificial Sequence
<220> FEATURE:
<223> OTHER INFORMATION: Expression from a synthetic gene

<400> SEQUENCE: 8

```
Met Ala Gln Leu Ser Lys Glu Ile Lys Phe Arg Lys Ile Glu Leu Lys
1               5                   10                  15

Glu Gly Thr Met Gly Pro Lys Ile Pro Gln Trp Pro Leu Thr Lys Glu
            20                  25                  30

Lys Leu Glu Gly Ala Lys Glu Ile Val Gln Arg Leu Leu Ser Glu Gly
        35                  40                  45

Lys Ile Ser Glu Ala Ser Asp Asn Asn Pro Tyr Asn Ser Pro Ile Phe
    50                  55                  60

Val Ile Lys Lys Arg Ser Gly Lys Trp Arg Leu Leu Gln Asp Leu Arg
65                  70                  75                  80

Glu Leu Asn Lys Thr Val Gln Val Gly Thr Glu Ile Ser Arg Gly Leu
                85                  90                  95

Pro His Pro Gly Gly Leu Ile Lys Cys Lys His Met Thr Val Leu Asp
            100                 105                 110

Ile Gly Asp Ala Tyr Phe Thr Ile Pro Leu Asp Pro Glu Phe Arg Pro
        115                 120                 125

Tyr Thr Ala Phe Thr Ile Pro Ser Ile Asn His Gln Glu Pro Asp Lys
    130                 135                 140

Arg Tyr Val Trp Asn Cys Leu Pro Gln Gly Phe Val Leu Ser Pro Tyr
145                 150                 155                 160

Ile Tyr Gln Lys Thr Leu Gln Glu Ile Leu Gln Pro Phe Arg Glu Arg
                165                 170                 175

Tyr Pro Glu Val Gln Leu Tyr Gln Tyr Met Asp Asp Leu Phe Val Gly
            180                 185                 190

Ser Asn Gly Ser Lys Lys Gln His Lys Glu Leu Ile Ile Glu Leu Arg
        195                 200                 205

Ala Ile Leu Leu Glu Lys Gly Phe Glu Thr Pro Asp Asp Lys Leu Gln
    210                 215                 220

Glu Val Pro Pro Tyr Ser Trp Leu Gly Tyr Gln Leu Cys Pro Glu Asn
225                 230                 235                 240

Trp Lys Val Gln Lys Met Gln Leu Asp Met Val Lys Asn Pro Thr Leu
                245                 250                 255

Asn Asp Val Gln Lys Leu Val Gly Lys Ile Asn Trp Ala Ser Gln Gly
            260                 265                 270

Val Pro Gly Leu Thr Val Lys His Ile Ala Ala Thr Thr Lys Gly Cys
        275                 280                 285

Leu Glu Leu Asn Gln Lys Val Ile Trp Thr Glu Glu Ala Gln Lys Glu
    290                 295                 300

Leu Glu Glu Asn Asn Glu Lys Ile Lys Asn Ala Gln Gly Leu Gln Tyr
305                 310                 315                 320

Tyr Asn Pro Glu Glu Met Leu Cys Glu Val Glu Ile Thr Lys Asn
                325                 330                 335

Tyr Glu Ala Thr Tyr Val Ile Lys Gln Ser Gln Gly Ile Leu Trp Ala
            340                 345                 350

Gly Lys Lys Ile Met Lys Ala Asn Lys Gly Trp Ser Thr Val Lys Asn
        355                 360                 365

Leu Met Leu Leu Leu Gln His Val Ala Thr Glu Ser Ile Thr Arg Val
    370                 375                 380

Gly Lys Cys Pro Thr Phe Lys Val Pro Phe Thr Lys Glu Gln Val Met
385                 390                 395                 400
```

Trp Glu Met Gln Lys Gly Trp Tyr Tyr Ser Trp Leu Pro Glu Ile Val
            405                 410                 415

Tyr Thr His Gln Val Val His Asp Asp Trp Arg Met Lys Leu Val Glu
        420                 425                 430

Glu Pro Thr Ser Gly Ile Thr Ile Tyr Thr Gly Gly Gly Lys Gln Asn
            435                 440                 445

Gly Glu Gly Ile Ala Ala Tyr Val Thr Ser Asn Gly Arg Thr Lys Gln
        450                 455                 460

Lys Arg Leu Gly Pro Val Thr His Gln Val Ala Glu Arg Met Ala Ile
465                 470                 475                 480

Gln Met Ala Leu Glu Asp Thr Arg Asp Lys Gln Val Asn Ile Val Thr
            485                 490                 495

Asp Ser Tyr Tyr Cys Trp Lys Asn Ile Thr Glu Gly Leu Gly Leu Glu
        500                 505                 510

Gly Pro Gln Ser Pro Trp Trp Pro Ile Ile Gln Asn Ile Arg Glu Lys
        515                 520                 525

Glu Ile Val Tyr Phe Ala Trp Val Pro Gly His Lys Gly Ile Cys Gly
        530                 535                 540

Asn Gln Leu Ala Asp Glu Ala Ala Lys Ile Lys Glu Glu Ile
545                 550                 555

<210> SEQ ID NO 9
<211> LENGTH: 1674
<212> TYPE: DNA
<213> ORGANISM: Artificial Sequence
<220> FEATURE:
<221> NAME/KEY: source
<222> LOCATION: 1..1674
<223> OTHER INFORMATION: /mol_type="unassigned DNA"
      /note="Synthetic gene"
      /organism="Artificial Sequence"

<400> SEQUENCE: 9

```
atggcacagc tgagcaaaga aatcaaattt cgcaaaatcg aactgaaaga aggcaccatg      60
ggtccgaaaa ttccgcagtg gcctctgacc aaagaaaaac tggaaggtgc aaaagaaatt     120
gttcagcgtc tgctgagcga aggtaaaatt agcgaagcaa cgataataa cccgtataac      180 agcccgattt tcgtgatcaa aaaacgtagc ggtaaatggc gtctgctgca ggatctgcgt     240
gaactgaata aaaccgttca ggttggcacc gaaattagcc gtggtctgcc gcatccgggt     300
ggtctgatta atgtaaaaca catgaccgtt ctggatattg cgacgcata ttttaccatt      360 ccgctggatc cggaatttcg tccgtatacc gcatttacaa ttccgagcat taatcatcaa     420
gaaccggata acgttatgt gtggaattgc ctgccgcagg gttttgttct gagcccgtat      480
atctatcaga aaacgctgca agaaattctg cagccatttc gtgaacgtta tccggaagtt     540
cagctgtatc agtatatgga tgacctgttt gtgggtagca atggtagcaa aaacagcac      600 aaagaactga tcattgaact gcgtgcaatt ctgctggaaa aggttttga acaccggat       660 gataaactgc aagaagttcc gccttatagc tggctgggtt atcagctgtg tccggaaaat     720
tggaaagttc agaaaatgca gctggatatg gttaaaaatc gaccctgaa tgatgtgcag      780 aaactggtgg gcaaaattaa ttgggctagc cagggtgttc cggtctgac cgttaaacat      840 attgcagcaa ccaccaaagg ttgtctggaa ctgaatcaga agttatctg gaccgaagaa      900 gcacaaaaag aactggaaga aacaacgag aaaatcaaaa atgcacaggg cctgcagtat      960
tataacccgg aagaagaaat gctttgcgaa gtggaaatca ccaaaaacta tgaagccacc    1020
```

-continued

```
tatgtgatta acagagcca gggtattctg tgggcaggca aaaaggcat gaaagccgct    1080 aaaaccaaaa gcaccgtgaa aaatctgatg ctgctgctgc aacatgtggc aaccgaaagc    1140 attaccegtg ttggtaaatg tccgaccttt aaagttccgt ttaccaaaga acaggtgatg    1200
tgggaaatgc agaaaggttg gtattatagt tggctgccgg aaattgttta tacccatcag    1260
gttgttcatg atgactggcg tatgaaactg gttgaagaac cgaccagcgg tattaccatt    1320
tataccggtg gtggtaaaca gaatggtgaa ggtattgcag cctatgttac agcaatggt    1380 cgtaccaaac agaaacgtct gggtccggtt acacatcagg tggcagaacg tatggcaatt    1440
cagatggcac tggaagatac ccgtgataaa caggttaata ttgtgaccga tagctattat    1500
tgttggaaaa acattaccga aggtctgggt ctggaaggtc cgcagagccc gtggtggccg    1560
attattcaga atattcgcga aaagaaaatc gtgtactttg catgggttcc aggtcataaa    1620
ggtatttgtg gtaatcagct ggcagatgaa gcagccaaaa tcaaagaaga gatc    1674
```

<210> SEQ ID NO 10
<211> LENGTH: 558
<212> TYPE: PRT
<213> ORGANISM: Artificial Sequence
<220> FEATURE:
<223> OTHER INFORMATION: Expression from a synthetic gene

<400> SEQUENCE: 10

```
Met Ala Gln Leu Ser Lys Glu Ile Lys Phe Arg Lys Ile Glu Leu Lys
1               5                   10                  15

Glu Gly Thr Met Gly Pro Lys Ile Pro Gln Trp Pro Leu Thr Lys Glu
            20                  25                  30

Lys Leu Glu Gly Ala Lys Glu Ile Val Gln Arg Leu Leu Ser Glu Gly
        35                  40                  45

Lys Ile Ser Glu Ala Ser Asp Asn Asn Pro Tyr Asn Ser Pro Ile Phe
    50                  55                  60

Val Ile Lys Lys Arg Ser Gly Lys Trp Arg Leu Leu Gln Asp Leu Arg
65                  70                  75                  80

Glu Leu Asn Lys Thr Val Gln Val Gly Thr Glu Ile Ser Arg Gly Leu
                85                  90                  95

Pro His Pro Gly Gly Leu Ile Lys Cys Lys His Met Thr Val Leu Asp
            100                 105                 110

Ile Gly Asp Ala Tyr Phe Thr Ile Pro Leu Asp Pro Glu Phe Arg Pro
        115                 120                 125

Tyr Thr Ala Phe Thr Ile Pro Ser Ile Asn His Gln Glu Pro Asp Lys
    130                 135                 140

Arg Tyr Val Trp Asn Cys Leu Pro Gln Gly Phe Val Leu Ser Pro Tyr
145                 150                 155                 160

Ile Tyr Gln Lys Thr Leu Gln Glu Ile Leu Gln Pro Phe Arg Glu Arg
                165                 170                 175

Tyr Pro Glu Val Gln Leu Tyr Gln Tyr Met Asp Asp Leu Phe Val Gly
            180                 185                 190

Ser Asn Gly Ser Lys Lys Gln His Lys Glu Leu Ile Ile Glu Leu Arg
        195                 200                 205

Ala Ile Leu Leu Glu Lys Gly Phe Glu Thr Pro Asp Asp Lys Leu Gln
    210                 215                 220

Glu Val Pro Pro Tyr Ser Trp Leu Gly Tyr Gln Leu Cys Pro Glu Asn
225                 230                 235                 240

Trp Lys Val Gln Lys Met Gln Leu Asp Met Val Lys Asn Pro Thr Leu
                245                 250                 255
```

Asn Asp Val Gln Lys Leu Val Gly Lys Ile Asn Trp Ala Ser Gln Gly
        260                 265                 270

Val Pro Gly Leu Thr Val Lys His Ile Ala Ala Thr Lys Gly Cys
        275                 280                 285

Leu Glu Leu Asn Gln Lys Val Ile Trp Thr Glu Glu Ala Gln Lys Glu
290                 295                 300

Leu Glu Glu Asn Glu Lys Ile Lys Asn Ala Gln Gly Leu Gln Tyr
305                 310                 315                 320

Tyr Asn Pro Glu Glu Glu Met Leu Cys Glu Val Ile Thr Lys Asn
                325                 330                 335

Tyr Glu Ala Thr Tyr Val Ile Lys Gln Ser Gln Gly Ile Leu Trp Ala
        340                 345                 350

Gly Lys Lys Gly Met Lys Ala Ala Lys Thr Lys Ser Thr Val Lys Asn
                355                 360                 365

Leu Met Leu Leu Leu Gln His Val Ala Thr Glu Ser Ile Thr Arg Val
        370                 375                 380

Gly Lys Cys Pro Thr Phe Lys Val Pro Phe Thr Lys Glu Gln Val Met
385                 390                 395                 400

Trp Glu Met Gln Lys Gly Trp Tyr Tyr Ser Trp Leu Pro Glu Ile Val
                405                 410                 415

Tyr Thr His Gln Val Val His Asp Asp Trp Arg Met Lys Leu Val Glu
        420                 425                 430

Glu Pro Thr Ser Gly Ile Thr Ile Tyr Thr Gly Gly Lys Gln Asn
                435                 440                 445

Gly Glu Gly Ile Ala Ala Tyr Val Thr Ser Asn Gly Arg Thr Lys Gln
        450                 455                 460

Lys Arg Leu Gly Pro Val Thr His Gln Val Ala Glu Arg Met Ala Ile
465                 470                 475                 480

Gln Met Ala Leu Glu Asp Thr Arg Asp Lys Gln Val Asn Ile Val Thr
                485                 490                 495

Asp Ser Tyr Tyr Cys Trp Lys Asn Ile Thr Glu Gly Leu Gly Leu Glu
        500                 505                 510

Gly Pro Gln Ser Pro Trp Trp Pro Ile Ile Gln Asn Ile Arg Glu Lys
                515                 520                 525

Glu Ile Val Tyr Phe Ala Trp Val Pro Gly His Lys Gly Ile Cys Gly
        530                 535                 540

Asn Gln Leu Ala Asp Glu Ala Ala Lys Ile Lys Glu Glu Ile
545                 550                 555

```
<210> SEQ ID NO 11
<211> LENGTH: 1674
<212> TYPE: DNA
<213> ORGANISM: Artificial Sequence
<220> FEATURE:
<221> NAME/KEY: source
<222> LOCATION: 1..1674
<223> OTHER INFORMATION: /mol_type="unassigned DNA"
      /note="Synthetic gene"
      /organism="Artificial Sequence"

<400> SEQUENCE: 11
atggcacagc tgagcaaaga aatcaaattt cgcaaaatcg aactgaaaga aggcaccatg     60
ggtccgaaaa ttccgcagtg gcctctgacc aaagaaaaac tggaaggtgc aaaagaaatt    120
gttcagcgtc tgctgagcga aggtaaaatt agcgaagcaa gcgataataa cccgtataac    180
agcccgattt tcgtgatcaa aaaacgtagc ggtaaatggc gtctgctgca ggatctgcgt    240
```

```
gaactgaata aaaccgttca ggttggcacc gaaattagcc gtggtctgcc gcatccgggt    300
ggtctgatta aatgtaaaca catgaccgtt ctggatattg cgacgcata ttttaccatt     360 ccgctggatc cggaatttcg tccgtatacc gcatttacaa ttccgagcat taatcatcaa   420
gaaccggata acgttatgt gtggaattgc ctgccgcagg gttttgttct gagcccgtat   480
atctatcaga aaacgctgca agaaattctg cagccatttc gtgaacgtta tccggaagtt   540
cagctgtatc agtatatgga tgacctgttt gtgggtagca atggtagcaa aaaacagcac   600
aaagaactga tcattgaact gcgtgcaatt ctgctggaaa aaggttttga acaccggat    660 gataaactgc aagaagttcc gccttatagc tggctgggtt atcagctgtg tccggaaaat   720
tggaaagttc agaaaatgca gctggatatg ttaaaaatc gaccctgaa tgatgtgcag    780 aaactggtgg gcaaaattaa ttgggctagc cagggtgttc cgggtctgac cgttaaacat   840
attgcagcaa ccaccaaagg ttgtctggaa ctgaatcaga aagttatctg gaccgaagaa   900
gcacaaaaag aactggaaga aaacaacgag aaaatcaaaa atgcacaggg cctgcagtat   960
tataacccgg aagaagaaat gctttgcgaa gtggaaatca ccaaaaacta tgaagccacc  1020
tatgtgatta acagagcca gggtattctg tgggcaggca aaaaaatcat gaaagccaat  1080
aaaggttgga gcaccgtgaa aaatctgatg ctgctgctgc aacatgtggc aaccgaaagc  1140 attaccgtg ttggtaaatg tccgaccttt aaagttccgt ttaccaaaga acaggtgatg   1200
tgggaaatgc agaaaggttg gtattatagt tggctgccgg aaattgttta tacccatcag  1260
gttgttcatg atgactggcg tatgaaactg gttgaagaac cgaccagcgg tattaccatt  1320
tataccggtg gtggtaaaca gaatggtgaa ggtattgcag cctatgttac cagcaatggt  1380
cgtaccaaac agaaacgtct gggtccggtt acacatcagg tggcagaacg tatggcaatt  1440
cagatggcac tggaagatac ccgtgataaa cgggttaata ttgtgaccga tagctattat  1500
tgttggaaaa acattaccga aggtctgggt ctggaaggtc gcagagccc gtggtggccg  1560 attattcaga atattcacga aaagaaatc gtgtactttg catgggttcc aggtcataaa  1620
ggtatttgtg gtaatcagct ggcagatgaa gcagccaaaa tcaaagaaga gatc         1674
```

<210> SEQ ID NO 12
<211> LENGTH: 558
<212> TYPE: PRT
<213> ORGANISM: Artificial Sequence
<220> FEATURE:
<223> OTHER INFORMATION: Expression from a synthetic gene

<400> SEQUENCE: 12

```
Met Ala Gln Leu Ser Lys Glu Ile Lys Phe Arg Lys Ile Glu Leu Lys
1               5                   10                  15

Glu Gly Thr Met Gly Pro Lys Ile Pro Gln Trp Pro Leu Thr Lys Glu
            20                  25                  30

Lys Leu Glu Gly Ala Lys Glu Ile Val Gln Arg Leu Leu Ser Glu Gly
        35                  40                  45

Lys Ile Ser Glu Ala Ser Asp Asn Asn Pro Tyr Asn Ser Pro Ile Phe
    50                  55                  60

Val Ile Lys Lys Arg Ser Gly Lys Trp Arg Leu Leu Gln Asp Leu Arg
65                  70                  75                  80

Glu Leu Asn Lys Thr Val Gln Val Gly Thr Glu Ile Ser Arg Gly Leu
                85                  90                  95

Pro His Pro Gly Gly Leu Ile Lys Cys Lys His Met Thr Val Leu Asp
            100                 105                 110
```

-continued

```
Ile Gly Asp Ala Tyr Phe Thr Ile Pro Leu Asp Pro Glu Phe Arg Pro
            115                 120                 125

Tyr Thr Ala Phe Thr Ile Pro Ser Ile Asn His Gln Glu Pro Asp Lys
        130                 135                 140

Arg Tyr Val Trp Asn Cys Leu Pro Gln Gly Phe Val Leu Ser Pro Tyr
145                 150                 155                 160

Ile Tyr Gln Lys Thr Leu Gln Glu Ile Leu Gln Pro Phe Arg Glu Arg
                165                 170                 175

Tyr Pro Glu Val Gln Leu Tyr Gln Tyr Met Asp Asp Leu Phe Val Gly
            180                 185                 190

Ser Asn Gly Ser Lys Lys Gln His Lys Glu Leu Ile Ile Glu Leu Arg
        195                 200                 205

Ala Ile Leu Leu Glu Lys Gly Phe Glu Thr Pro Asp Asp Lys Leu Gln
    210                 215                 220

Glu Val Pro Pro Tyr Ser Trp Leu Gly Tyr Gln Leu Cys Pro Glu Asn
225                 230                 235                 240

Trp Lys Val Gln Lys Met Gln Leu Asp Met Val Lys Asn Pro Thr Leu
                245                 250                 255

Asn Asp Val Gln Lys Leu Val Gly Lys Ile Asn Trp Ala Ser Gln Gly
            260                 265                 270

Val Pro Gly Leu Thr Val Lys His Ile Ala Ala Thr Thr Lys Gly Cys
        275                 280                 285

Leu Glu Leu Asn Gln Lys Val Ile Trp Thr Glu Glu Ala Gln Lys Glu
    290                 295                 300

Leu Glu Glu Asn Asn Glu Lys Ile Lys Asn Ala Gln Gly Leu Gln Tyr
305                 310                 315                 320

Tyr Asn Pro Glu Glu Glu Met Leu Cys Glu Val Glu Ile Thr Lys Asn
                325                 330                 335

Tyr Glu Ala Thr Tyr Val Ile Lys Gln Ser Gln Gly Ile Leu Trp Ala
            340                 345                 350

Gly Lys Lys Ile Met Lys Ala Asn Lys Gly Trp Ser Thr Val Lys Asn
        355                 360                 365

Leu Met Leu Leu Leu Gln His Val Ala Thr Glu Ser Ile Thr Arg Val
    370                 375                 380

Gly Lys Cys Pro Thr Phe Lys Val Pro Phe Thr Lys Glu Gln Val Met
385                 390                 395                 400

Trp Glu Met Gln Lys Gly Trp Tyr Tyr Ser Trp Leu Pro Glu Ile Val
                405                 410                 415

Tyr Thr His Gln Val Val His Asp Asp Trp Arg Met Lys Leu Val Glu
            420                 425                 430

Glu Pro Thr Ser Gly Ile Thr Ile Tyr Thr Gly Gly Lys Gln Asn
        435                 440                 445

Gly Glu Gly Ile Ala Ala Tyr Val Thr Ser Asn Gly Arg Thr Lys Gln
    450                 455                 460

Lys Arg Leu Gly Pro Val Thr His Gln Val Ala Glu Arg Met Ala Ile
465                 470                 475                 480

Gln Met Ala Leu Glu Asp Thr Arg Asp Lys Arg Val Asn Ile Val Thr
                485                 490                 495

Asp Ser Tyr Tyr Cys Trp Lys Asn Ile Thr Glu Gly Leu Gly Leu Glu
            500                 505                 510

Gly Pro Gln Ser Pro Trp Trp Pro Ile Ile Gln Asn Ile His Glu Lys
        515                 520                 525
```

```
Glu Ile Val Tyr Phe Ala Trp Val Pro Gly His Lys Gly Ile Cys Gly
        530                 535                 540

Asn Gln Leu Ala Asp Glu Ala Ala Lys Ile Lys Glu Glu Ile
545                 550                 555
```

<210> SEQ ID NO 13
<211> LENGTH: 1674
<212> TYPE: DNA
<213> ORGANISM: Artificial Sequence
<220> FEATURE:
<221> NAME/KEY: source
<222> LOCATION: 1..1674
<223> OTHER INFORMATION: /mol_type="unassigned DNA"
    /note="Synthetic gene"
    /organism="Artificial Sequence"

<400> SEQUENCE: 13

```
atggcacagc tgagcaaaga aatcaaattt cgcaaaatcg aactgaaaga aggcaccatg      60
ggtccgaaaa ttccgcagtg gcctctgacc aaagaaaaac tggaaggtgc aaaagaaatt     120
gttcagcgtc tgctgagcga aggtaaaatt agcgaagcaa gcgataataa cccgtataac     180
agcccgattt tcgtgatcaa aaaacgtagc ggtaaatggc gtctgctgca ggatctgcgt     240
gaactgaata aaaccgttca ggttggcacc gaaattagcc gtggtctgcc gcatccgggt     300
ggtctgatta aatgtaaaca catgaccgtt ctggatattg cgacgcata ttttaccatt      360
ccgctggatc cggaatttcg tccgtatacc gcatttacaa ttccgagcat taatcatcaa     420
gaaccggata acgttatgt gtggaattgc ctgccgcagg ttttgttct gagcccgtat       480
atctatcaga aaacgctgca agaaattctg cagccatttc gtgaacgtta tccggaagtt     540
cagctgtatc agtatatgga tgacctgttt gtgggtagca atggtagcaa aaaacagcac     600
aaagaactga tcattgaact gcgtgcaatt ctgctggaaa aaggttttga acaccggat      660
gataaactgc aagaagttcc gccttatagc tggctgggtt atcagctgtg tccggaaaat     720
tggaaagttc agaaaatgca gctggatatg gttaaaaatc cgaccctgaa tgatgtgcag     780
aaactggtgg caaaattaa ttgggctagc cagggtgttc cgggtctgac cgttaaacat     840
attgcagcaa ccaccaaagg ttgtctggaa ctgaatcaga agttatctg gaccgaagaa      900
gcacaaaaag aactggaaga aaacaacgag aaaatcaaaa atgcacaggg cctgcagtat     960
tataacccgg aagaagaaat gctttgcgaa gtggaaatca ccaaaaacta tgaagccacc    1020
tatgtgatta acagagcca gggtattctg tgggcaggca aaaaaggcat gaaagccgct    1080
aaaaccaaaa gcaccgtgaa aaatctgatg ctgctgctgc aacatgtggc aaccgaaagc    1140
attacccgtg ttggtaaatg tccgaccttt aaagttccgt ttaccaaaga caggtgatg    1200
tgggaaatgc agaaaggttg gtattatagt tggctgccgg aaattgttta tcccatcag    1260
gttgttcatg atgactggcg tatgaaactg gttgaagaac cgaccagcgg tattaccatt    1320
tataccggtg gtggtaaaca aatggtgaa ggtattgcag cctatgttac agcaatggt    1380
cgtaccaaac agaaacgtct gggtccggtt acacatcagg tggcagaacg tatggcaatt    1440
cagatggcac tggaagatac ccgtgataaa cgggttaata ttgtgaccga tagctattat    1500
tgttggaaaa acattaccga aggtctgggt ctggaaggtc gcagagccc gtggtggccg    1560
attattcaga atattcacga aaaagaaatc gtgtactttg catgggttcc aggtcataaa    1620
ggtatttgtg gtaatcagct ggcagatgaa gcagccaaaa tcaaagaaga gatc          1674
```

<210> SEQ ID NO 14
<211> LENGTH: 558

```
<212> TYPE: PRT
<213> ORGANISM: Artificial Sequence
<220> FEATURE:
<223> OTHER INFORMATION: Expression from a synthetic gene

<400> SEQUENCE: 14
```

| Met | Ala | Gln | Leu | Ser | Lys | Glu | Ile | Lys | Phe | Arg | Lys | Ile | Glu | Leu | Lys |
|---|---|---|---|---|---|---|---|---|---|---|---|---|---|---|---|
| 1 | | | | 5 | | | | | 10 | | | | | 15 | |

Glu Gly Thr Met Gly Pro Lys Ile Pro Gln Trp Pro Leu Thr Lys Glu
            20              25              30

Lys Leu Glu Gly Ala Lys Glu Ile Val Gln Arg Leu Leu Ser Glu Gly
        35              40              45

Lys Ile Ser Glu Ala Ser Asp Asn Asn Pro Tyr Asn Ser Pro Ile Phe
50              55              60

Val Ile Lys Lys Arg Ser Gly Lys Trp Arg Leu Leu Gln Asp Leu Arg
65              70              75              80

Glu Leu Asn Lys Thr Val Gln Val Gly Thr Glu Ile Ser Arg Gly Leu
        85              90              95

Pro His Pro Gly Gly Leu Ile Lys Cys Lys His Met Thr Val Leu Asp
            100            105            110

Ile Gly Asp Ala Tyr Phe Thr Ile Pro Leu Asp Pro Glu Phe Arg Pro
        115              120            125

Tyr Thr Ala Phe Thr Ile Pro Ser Ile Asn His Gln Glu Pro Asp Lys
        130              135            140

Arg Tyr Val Trp Asn Cys Leu Pro Gln Gly Phe Val Leu Ser Pro Tyr
145             150             155            160

Ile Tyr Gln Lys Thr Leu Gln Glu Ile Leu Gln Pro Phe Arg Glu Arg
            165            170            175

Tyr Pro Glu Val Gln Leu Tyr Gln Tyr Met Asp Asp Leu Phe Val Gly
        180              185            190

Ser Asn Gly Ser Lys Lys Gln His Lys Glu Leu Ile Ile Glu Leu Arg
        195              200            205

Ala Ile Leu Leu Glu Lys Gly Phe Glu Thr Pro Asp Asp Lys Leu Gln
    210              215            220

Glu Val Pro Pro Tyr Ser Trp Leu Gly Tyr Gln Leu Cys Pro Glu Asn
225             230            235            240

Trp Lys Val Gln Lys Met Gln Leu Asp Met Val Lys Asn Pro Thr Leu
            245            250            255

Asn Asp Val Gln Lys Leu Val Gly Lys Ile Asn Trp Ala Ser Gln Gly
        260              265            270

Val Pro Gly Leu Thr Val Lys His Ile Ala Ala Thr Thr Lys Gly Cys
        275              280            285

Leu Glu Leu Asn Gln Lys Val Ile Trp Thr Glu Glu Ala Gln Lys Glu
    290              295            300

Leu Glu Glu Asn Asn Glu Lys Ile Lys Asn Ala Gln Gly Leu Gln Tyr
305             310            315            320

Tyr Asn Pro Glu Glu Met Leu Cys Glu Val Glu Ile Thr Lys Asn
            325            330            335

Tyr Glu Ala Thr Tyr Val Ile Lys Gln Ser Gln Gly Ile Leu Trp Ala
            340            345            350

Gly Lys Lys Gly Met Lys Ala Ala Lys Thr Lys Ser Thr Val Lys Asn
        355              360            365

Leu Met Leu Leu Leu Gln His Val Ala Thr Glu Ser Ile Thr Arg Val
    370              375            380

-continued

Gly Lys Cys Pro Thr Phe Lys Val Pro Phe Thr Lys Glu Gln Val Met
385                 390                 395                 400

Trp Glu Met Gln Lys Gly Trp Tyr Tyr Ser Trp Leu Pro Glu Ile Val
            405                 410                 415

Tyr Thr His Gln Val Val His Asp Asp Trp Arg Met Lys Leu Val Glu
        420                 425                 430

Glu Pro Thr Ser Gly Ile Thr Ile Tyr Thr Gly Gly Lys Gln Asn
            435                 440                 445

Gly Glu Gly Ile Ala Ala Tyr Val Thr Ser Asn Gly Arg Thr Lys Gln
    450                 455                 460

Lys Arg Leu Gly Pro Val Thr His Gln Val Ala Glu Arg Met Ala Ile
465                 470                 475                 480

Gln Met Ala Leu Glu Asp Thr Arg Asp Lys Arg Val Asn Ile Val Thr
            485                 490                 495

Asp Ser Tyr Tyr Cys Trp Lys Asn Ile Thr Glu Gly Leu Gly Leu Glu
        500                 505                 510

Gly Pro Gln Ser Pro Trp Trp Pro Ile Ile Gln Asn Ile His Glu Lys
            515                 520                 525

Glu Ile Val Tyr Phe Ala Trp Val Pro Gly His Lys Gly Ile Cys Gly
        530                 535                 540

Asn Gln Leu Ala Asp Glu Ala Ala Lys Ile Lys Glu Ile
545                 550                 555

<210> SEQ ID NO 15
<211> LENGTH: 558
<212> TYPE: PRT
<213> ORGANISM: Artificial Sequence
<220> FEATURE:
<223> OTHER INFORMATION: Expression from a synthetic gene

<400> SEQUENCE: 15

Met Ala Gln Leu Ser Lys Glu Ile Lys Phe Arg Lys Ile Glu Leu Lys
1               5                   10                  15

Glu Gly Thr Met Gly Pro Lys Ile Pro Gln Trp Pro Leu Thr Lys Glu
            20                  25                  30

Lys Leu Glu Gly Ala Lys Glu Ile Val Gln Arg Leu Leu Ser Glu Gly
        35                  40                  45

Lys Ile Ser Glu Ala Ser Asp Asn Asn Pro Tyr Asn Ser Pro Ile Phe
    50                  55                  60

Val Ile Lys Lys Arg Ser Gly Lys Trp Arg Leu Leu Gln Asp Leu Arg
65                  70                  75                  80

Glu Leu Asn Lys Thr Val Gln Val Gly Thr Glu Ile Ser Arg Gly Leu
            85                  90                  95

Pro His Pro Gly Gly Leu Ile Lys Cys Lys His Met Thr Val Leu Asp
        100                 105                 110

Ile Gly Asp Ala Tyr Phe Thr Ile Pro Leu Asp Pro Glu Phe Arg Pro
    115                 120                 125

Tyr Thr Ala Phe Thr Ile Pro Ser Ile Asn His Gln Glu Pro Asp Lys
130                 135                 140

Arg Tyr Val Trp Asn Cys Leu Pro Gln Gly Phe Val Leu Ser Pro Tyr
145                 150                 155                 160

Ile Tyr Gln Lys Thr Leu Gln Glu Ile Leu Gln Pro Phe Arg Glu Arg
            165                 170                 175

Tyr Pro Glu Val Gln Leu Tyr Gln Tyr Met Asp Asp Leu Phe Val Gly
        180                 185                 190

```
Ser Asn Gly Ser Lys Lys Gln His Lys Glu Leu Ile Ile Glu Leu Arg
            195                 200                 205

Ala Ile Leu Leu Glu Lys Gly Phe Glu Thr Pro Asp Asp Lys Leu Gln
210                 215                 220

Glu Val Pro Pro Tyr Ser Trp Leu Gly Tyr Gln Leu Cys Pro Glu Asn
225                 230                 235                 240

Trp Lys Val Gln Lys Met Gln Leu Asp Met Val Lys Asn Pro Thr Leu
                245                 250                 255

Asn Asp Val Gln Lys Leu Val Gly Lys Ile Asn Trp Ala Ser Gln Gly
            260                 265                 270

Val Pro Gly Leu Thr Val Lys His Ile Ala Ala Thr Thr Lys Gly Cys
        275                 280                 285

Leu Glu Leu Asn Gln Lys Val Ile Trp Thr Glu Glu Ala Gln Lys Glu
    290                 295                 300

Leu Glu Glu Asn Asn Glu Lys Ile Lys Asn Ala Gln Gly Leu Gln Tyr
305                 310                 315                 320

Tyr Asn Pro Glu Glu Met Leu Cys Glu Val Glu Ile Thr Lys Asn
                325                 330                 335

Tyr Glu Ala Thr Tyr Val Ile Lys Gln Ser Gln Gly Ile Leu Trp Ala
            340                 345                 350

Gly Lys Lys Gly Met Lys Ala Ala Lys Thr Asn Ser Thr Val Lys Asn
        355                 360                 365

Leu Met Leu Leu Leu Gln His Val Ala Thr Glu Ser Ile Thr Arg Val
    370                 375                 380

Gly Lys Cys Pro Thr Phe Lys Val Pro Phe Thr Lys Glu Gln Val Met
385                 390                 395                 400

Trp Glu Met Gln Lys Gly Trp Tyr Tyr Ser Trp Leu Pro Glu Ile Val
                405                 410                 415

Tyr Thr His Gln Val Val His Asp Asp Trp Arg Met Lys Leu Val Glu
            420                 425                 430

Glu Pro Thr Ser Gly Ile Thr Ile Tyr Thr Gly Gly Lys Gln Asn
        435                 440                 445

Gly Glu Gly Ile Ala Ala Tyr Val Thr Ser Asn Gly Arg Thr Lys Gln
450                 455                 460

Lys Arg Leu Gly Pro Val Thr His Gln Val Ala Glu Arg Met Ala Ile
465                 470                 475                 480

Gln Met Ala Leu Glu Asp Thr Arg Asp Lys Gln Val Asn Ile Val Thr
                485                 490                 495

Asp Ser Tyr Tyr Cys Trp Lys Asn Ile Thr Glu Gly Leu Gly Leu Glu
            500                 505                 510

Gly Pro Gln Ser Pro Trp Trp Pro Ile Ile Gln Asn Ile Arg Glu Lys
        515                 520                 525

Glu Ile Val Tyr Phe Ala Trp Val Pro Gly His Lys Gly Ile Cys Gly
    530                 535                 540

Asn Gln Leu Ala Asp Glu Ala Ala Lys Ile Lys Glu Glu Ile
545                 550                 555

<210> SEQ ID NO 16
<211> LENGTH: 558
<212> TYPE: PRT
<213> ORGANISM: Artificial Sequence
<220> FEATURE:
<223> OTHER INFORMATION: Expression from a synthetic gene

<400> SEQUENCE: 16
```

```
Met Ala Gln Leu Ser Lys Glu Ile Lys Phe Arg Lys Ile Glu Leu Lys
1               5                   10                  15

Glu Gly Thr Met Gly Pro Lys Ile Pro Gln Trp Pro Leu Thr Lys Glu
            20                  25                  30

Lys Leu Glu Gly Ala Lys Glu Ile Val Gln Arg Leu Leu Ser Glu Gly
        35                  40                  45

Lys Ile Ser Glu Ala Ser Asp Asn Asn Pro Tyr Asn Ser Pro Ile Phe
    50                  55                  60

Val Ile Lys Lys Arg Ser Gly Lys Trp Arg Leu Leu Gln Asp Leu Arg
65                  70                  75                  80

Glu Leu Asn Lys Thr Val Gln Val Gly Thr Glu Ile Ser Arg Gly Leu
                85                  90                  95

Pro His Pro Gly Gly Leu Ile Lys Cys Lys His Met Thr Val Leu Asp
            100                 105                 110

Ile Gly Asp Ala Tyr Phe Thr Ile Pro Leu Asp Pro Glu Phe Arg Pro
        115                 120                 125

Tyr Thr Ala Phe Thr Ile Pro Ser Ile Asn His Gln Glu Pro Asp Lys
    130                 135                 140

Arg Tyr Val Trp Asn Cys Leu Pro Gln Gly Phe Val Leu Ser Pro Tyr
145                 150                 155                 160

Ile Tyr Gln Lys Thr Leu Gln Glu Ile Leu Gln Pro Phe Arg Glu Arg
                165                 170                 175

Tyr Pro Glu Val Gln Leu Tyr Gln Tyr Met Asp Asp Leu Phe Val Gly
            180                 185                 190

Ser Asn Gly Ser Lys Lys Gln His Lys Glu Leu Ile Ile Glu Leu Arg
        195                 200                 205

Ala Ile Leu Leu Glu Lys Gly Phe Glu Thr Pro Asp Asp Lys Leu Gln
    210                 215                 220

Glu Val Pro Pro Tyr Ser Trp Leu Gly Tyr Gln Leu Cys Pro Glu Asn
225                 230                 235                 240

Trp Lys Val Gln Lys Met Gln Leu Asp Met Val Lys Asn Pro Thr Leu
                245                 250                 255

Asn Asp Val Gln Lys Leu Val Gly Lys Ile Asn Trp Ala Ser Gln Gly
            260                 265                 270

Val Pro Gly Leu Thr Val Lys His Ile Ala Ala Thr Lys Gly Cys
        275                 280                 285

Leu Glu Leu Asn Gln Lys Val Ile Trp Thr Glu Glu Ala Gln Lys Glu
290                 295                 300

Leu Glu Glu Asn Glu Lys Ile Lys Asn Ala Gln Gly Leu Gln Tyr
305                 310                 315                 320

Tyr Asn Pro Glu Glu Glu Met Leu Cys Glu Val Glu Ile Thr Lys Asn
            325                 330                 335

Tyr Glu Ala Thr Tyr Val Ile Lys Gln Ser Gln Gly Ile Leu Trp Ala
        340                 345                 350

Gly Lys Lys Asp Met Lys Ala Ala Lys Thr Lys Ser Thr Val Lys Asn
    355                 360                 365

Leu Met Leu Leu Leu Gln His Val Ala Thr Glu Ser Ile Thr Arg Val
370                 375                 380

Gly Lys Cys Pro Thr Phe Lys Val Pro Phe Thr Lys Glu Gln Val Met
385                 390                 395                 400

Trp Glu Met Gln Lys Gly Trp Tyr Tyr Ser Trp Leu Pro Glu Ile Val
                405                 410                 415

Tyr Thr His Gln Val Val His Asp Asp Trp Arg Met Lys Leu Val Glu
```

```
                      420                 425                 430
Glu Pro Thr Ser Gly Ile Thr Ile Tyr Thr Gly Gly Lys Gln Asn
                435                 440                 445
Gly Glu Gly Ile Ala Ala Tyr Val Thr Ser Asn Gly Arg Thr Lys Gln
            450                 455                 460
Lys Arg Leu Gly Pro Val Thr His Gln Val Ala Glu Arg Met Ala Ile
465                 470                 475                 480
Gln Met Ala Leu Glu Asp Thr Arg Asp Lys Gln Val Asn Ile Val Thr
                485                 490                 495
Asp Ser Tyr Tyr Cys Trp Lys Asn Ile Thr Glu Gly Leu Gly Leu Glu
                500                 505                 510
Gly Pro Gln Ser Pro Trp Trp Pro Ile Ile Gln Asn Ile Arg Glu Lys
            515                 520                 525
Glu Ile Val Tyr Phe Ala Trp Val Pro Gly His Lys Gly Ile Cys Gly
                530                 535                 540
Asn Gln Leu Ala Asp Glu Ala Ala Lys Ile Lys Glu Glu Ile
545                 550                 555

<210> SEQ ID NO 17
<211> LENGTH: 558
<212> TYPE: PRT
<213> ORGANISM: Artificial Sequence
<220> FEATURE:
<223> OTHER INFORMATION: Expression from a synthetic gene

<400> SEQUENCE: 17

Met Ala Gln Leu Ser Lys Glu Ile Lys Phe Arg Lys Ile Glu Leu Lys
1               5                   10                  15
Glu Gly Thr Met Gly Pro Lys Ile Pro Gln Trp Pro Leu Thr Lys Glu
                20                  25                  30
Lys Leu Glu Gly Ala Lys Glu Ile Val Gln Arg Leu Leu Ser Glu Gly
            35                  40                  45
Lys Ile Ser Glu Ala Ser Asp Asn Asn Pro Tyr Asn Ser Pro Ile Phe
        50                  55                  60
Val Ile Lys Lys Arg Ser Gly Lys Trp Arg Leu Leu Gln Asp Leu Arg
65                  70                  75                  80
Glu Leu Asn Lys Thr Val Gln Val Gly Thr Glu Ile Ser Arg Gly Leu
                85                  90                  95
Pro His Pro Gly Gly Leu Ile Lys Cys Lys His Met Thr Val Leu Asp
                100                 105                 110
Ile Gly Asp Ala Tyr Phe Thr Ile Pro Leu Asp Pro Glu Phe Arg Pro
            115                 120                 125
Tyr Thr Ala Phe Thr Ile Pro Ser Ile Asn His Gln Glu Pro Asp Lys
        130                 135                 140
Arg Tyr Val Trp Asn Cys Leu Pro Gln Gly Phe Val Leu Ser Pro Tyr
145                 150                 155                 160
Ile Tyr Gln Lys Thr Leu Gln Glu Ile Leu Gln Pro Phe Arg Glu Arg
                165                 170                 175
Tyr Pro Glu Val Gln Leu Tyr Gln Tyr Met Asp Asp Leu Phe Val Gly
                180                 185                 190
Ser Asn Gly Ser Lys Lys Gln His Lys Glu Leu Ile Ile Glu Leu Arg
            195                 200                 205
Ala Ile Leu Leu Glu Lys Gly Phe Glu Thr Pro Asp Asp Lys Leu Gln
        210                 215                 220
Glu Val Pro Pro Tyr Ser Trp Leu Gly Tyr Gln Leu Cys Pro Glu Asn
```

```
            225                 230                 235                 240

Trp Lys Val Gln Lys Met Gln Leu Asp Met Val Lys Asn Pro Thr Leu
            245                 250                 255

Asn Asp Val Gln Lys Leu Val Gly Lys Ile Asn Trp Ala Ser Gln Gly
            260                 265                 270

Val Pro Gly Leu Thr Val Lys His Ile Ala Ala Thr Lys Gly Cys
            275                 280                 285

Leu Glu Leu Asn Gln Lys Val Ile Trp Thr Glu Glu Ala Gln Lys Glu
            290                 295                 300

Leu Glu Glu Asn Glu Lys Ile Lys Asn Ala Gln Gly Leu Gln Tyr
305                 310                 315                 320

Tyr Asn Pro Glu Glu Glu Met Leu Cys Glu Val Ile Thr Lys Asn
            325                 330                 335

Tyr Glu Ala Thr Tyr Val Ile Lys Gln Ser Gln Gly Ile Leu Trp Ala
            340                 345                 350

Gly Lys Lys Asn Met Lys Ala Ala Lys Asn Ile Ser Thr Val Lys Asn
            355                 360                 365

Leu Met Leu Leu Leu Gln His Val Ala Thr Glu Ser Ile Thr Arg Val
            370                 375                 380

Gly Lys Cys Pro Thr Phe Lys Val Pro Phe Thr Lys Glu Gln Val Met
385                 390                 395                 400

Trp Glu Met Gln Lys Gly Trp Tyr Tyr Ser Trp Leu Pro Glu Ile Val
            405                 410                 415

Tyr Thr His Gln Val Val His Asp Asp Trp Arg Met Lys Leu Val Glu
            420                 425                 430

Glu Pro Thr Ser Gly Ile Thr Ile Tyr Thr Gly Gly Lys Gln Asn
            435                 440                 445

Gly Glu Gly Ile Ala Ala Tyr Val Thr Ser Asn Gly Arg Thr Lys Gln
            450                 455                 460

Lys Arg Leu Gly Pro Val Thr His Gln Val Ala Glu Arg Met Ala Ile
465                 470                 475                 480

Gln Met Ala Leu Glu Asp Thr Arg Asp Lys Gln Val Asn Ile Val Thr
            485                 490                 495

Asp Ser Tyr Tyr Cys Trp Lys Asn Ile Thr Glu Gly Leu Gly Leu Glu
            500                 505                 510

Gly Pro Gln Ser Pro Trp Trp Pro Ile Ile Gln Asn Ile Arg Glu Lys
            515                 520                 525

Glu Ile Val Tyr Phe Ala Trp Val Pro Gly His Lys Gly Ile Cys Gly
            530                 535                 540

Asn Gln Leu Ala Asp Glu Ala Ala Lys Ile Lys Glu Glu Ile
545                 550                 555

<210> SEQ ID NO 18
<211> LENGTH: 558
<212> TYPE: PRT
<213> ORGANISM: Artificial Sequence
<220> FEATURE:
<223> OTHER INFORMATION: Expression from a synthetic gene

<400> SEQUENCE: 18

Met Ala Gln Leu Ser Lys Glu Ile Lys Phe Arg Lys Ile Glu Leu Lys
1               5                   10                  15

Glu Gly Thr Met Gly Pro Lys Ile Pro Gln Trp Pro Leu Thr Lys Glu
            20                  25                  30

Lys Leu Glu Gly Ala Lys Glu Ile Val Gln Arg Leu Leu Ser Glu Gly
```

```
                 35                  40                  45
Lys Ile Ser Glu Ala Ser Asp Asn Asn Pro Tyr Asn Ser Pro Ile Phe
 50                  55                  60

Val Ile Lys Lys Arg Ser Gly Lys Trp Arg Leu Leu Gln Asp Leu Arg
 65                  70                  75                  80

Glu Leu Asn Lys Thr Val Gln Val Gly Thr Glu Ile Ser Arg Gly Leu
                 85                  90                  95

Pro His Pro Gly Gly Leu Ile Lys Cys Lys His Met Thr Val Leu Asp
                100                 105                 110

Ile Gly Asp Ala Tyr Phe Thr Ile Pro Leu Asp Pro Glu Phe Arg Pro
                115                 120                 125

Tyr Thr Ala Phe Thr Ile Pro Ser Ile Asn His Gln Glu Pro Asp Lys
                130                 135                 140

Arg Tyr Val Trp Asn Cys Leu Pro Gln Gly Phe Val Leu Ser Pro Tyr
145                 150                 155                 160

Ile Tyr Gln Lys Thr Leu Gln Glu Ile Leu Gln Pro Phe Arg Glu Arg
                165                 170                 175

Tyr Pro Glu Val Gln Leu Tyr Gln Tyr Met Asp Asp Leu Phe Val Gly
                180                 185                 190

Ser Asn Gly Ser Lys Lys Gln His Lys Glu Leu Ile Ile Glu Leu Arg
                195                 200                 205

Ala Ile Leu Leu Glu Lys Gly Phe Glu Thr Pro Asp Asp Lys Leu Gln
                210                 215                 220

Glu Val Pro Pro Tyr Ser Trp Leu Gly Tyr Gln Leu Cys Pro Glu Asn
225                 230                 235                 240

Trp Lys Val Gln Lys Met Gln Leu Asp Met Val Lys Asn Pro Thr Leu
                245                 250                 255

Asn Asp Val Gln Lys Leu Val Gly Lys Ile Asn Trp Ala Ser Gln Gly
                260                 265                 270

Val Pro Gly Leu Thr Val Lys His Ile Ala Ala Thr Thr Lys Gly Cys
                275                 280                 285

Leu Glu Leu Asn Gln Lys Val Ile Trp Thr Glu Glu Ala Gln Lys Glu
                290                 295                 300

Leu Glu Glu Asn Asn Glu Lys Ile Lys Asn Ala Gln Gly Leu Gln Tyr
305                 310                 315                 320

Tyr Asn Pro Glu Glu Met Leu Cys Glu Val Glu Ile Thr Lys Asn
                325                 330                 335

Tyr Glu Ala Thr Tyr Val Ile Lys Gln Ser Gln Gly Ile Leu Trp Ala
                340                 345                 350

Gly Lys Lys Ile Met Lys Ala Asn Lys Gly Trp Ser Thr Val Lys Asn
                355                 360                 365

Leu Met Leu Leu Gln His Val Ala Thr Glu Ser Ile Thr Arg Val
                370                 375                 380

Gly Lys Cys Pro Thr Phe Lys Val Pro Phe Thr Lys Glu Gln Val Met
385                 390                 395                 400

Trp Glu Met Gln Lys Gly Trp Tyr Tyr Ser Trp Leu Pro Glu Ile Val
                405                 410                 415

Tyr Thr His Gln Val Val His Asp Asp Trp Arg Met Lys Leu Val Glu
                420                 425                 430

Glu Pro Thr Ser Gly Ile Thr Ile Tyr Thr Gly Gly Lys Gln Asn
                435                 440                 445

Gly Glu Gly Ile Ala Ala Tyr Val Thr Ser Asn Gly Arg Thr Lys Gln
450                 455                 460
```

Lys Arg Leu Gly Pro Val Thr His Gln Val Ala Glu Arg Met Ala Ile
465                 470                 475                 480

Gln Met Ala Leu Glu Asp Thr Arg Asp Lys Arg Val Asn Ile Val Thr
                485                 490                 495

Asp Ser Tyr Tyr Cys Trp Lys Asn Ile Thr Glu Gly Leu Gly Leu Glu
            500                 505                 510

Gly Pro Gln Ser Pro Trp Trp Pro Ile Ile Gln Asn Ile Arg Glu Lys
        515                 520                 525

Glu Ile Val Tyr Phe Ala Trp Val Pro Gly His Lys Gly Ile Cys Gly
    530                 535                 540

Asn Gln Leu Ala Asp Ala Ala Arg Ile Lys Glu Glu Ile
545                 550                 555

<210> SEQ ID NO 19
<211> LENGTH: 558
<212> TYPE: PRT
<213> ORGANISM: Artificial Sequence
<220> FEATURE:
<223> OTHER INFORMATION: Expression from a synthetic gene

<400> SEQUENCE: 19

Met Ala Gln Leu Ser Lys Glu Ile Lys Phe Arg Lys Ile Glu Leu Lys
1               5                   10                  15

Glu Gly Thr Met Gly Pro Lys Ile Pro Gln Trp Pro Leu Thr Lys Glu
            20                  25                  30

Lys Leu Glu Gly Ala Lys Glu Ile Val Gln Arg Leu Leu Ser Glu Gly
        35                  40                  45

Lys Ile Ser Glu Ala Ser Asp Asn Asn Pro Tyr Asn Ser Pro Ile Phe
    50                  55                  60

Val Ile Lys Lys Arg Ser Gly Lys Trp Arg Leu Leu Gln Asp Leu Arg
65                  70                  75                  80

Glu Leu Asn Lys Thr Val Gln Val Gly Thr Glu Ile Ser Arg Gly Leu
                85                  90                  95

Pro His Pro Gly Gly Leu Ile Lys Cys Lys His Met Thr Val Leu Asp
            100                 105                 110

Ile Gly Asp Ala Tyr Phe Thr Ile Pro Leu Asp Pro Glu Phe Arg Pro
        115                 120                 125

Tyr Thr Ala Phe Thr Ile Pro Ser Ile Asn His Gln Glu Pro Asp Lys
    130                 135                 140

Arg Tyr Val Trp Asn Cys Leu Pro Gln Gly Phe Val Leu Ser Pro Tyr
145                 150                 155                 160

Ile Tyr Gln Lys Thr Leu Gln Glu Ile Leu Gln Pro Phe Arg Glu Arg
                165                 170                 175

Tyr Pro Glu Val Gln Leu Tyr Gln Tyr Met Asp Asp Leu Phe Val Gly
            180                 185                 190

Ser Asn Gly Ser Lys Lys Gln His Lys Glu Leu Ile Ile Glu Leu Arg
        195                 200                 205

Ala Ile Leu Leu Glu Lys Gly Phe Glu Thr Pro Asp Asp Lys Leu Gln
    210                 215                 220

Glu Val Pro Pro Tyr Ser Trp Leu Gly Tyr Gln Leu Cys Pro Glu Asn
225                 230                 235                 240

Trp Lys Val Gln Lys Met Gln Leu Asp Met Val Lys Asn Pro Thr Leu
                245                 250                 255

Asn Asp Val Gln Lys Leu Val Gly Lys Ile Asn Trp Ala Ser Gln Gly
            260                 265                 270

```
Val Pro Gly Leu Thr Val Lys His Ile Ala Ala Thr Thr Lys Gly Cys
        275                 280                 285

Leu Glu Leu Asn Gln Lys Val Ile Trp Thr Glu Glu Ala Gln Lys Glu
        290                 295                 300

Leu Glu Glu Asn Asn Glu Lys Ile Lys Asn Ala Gln Gly Leu Gln Tyr
305                 310                 315                 320

Tyr Asn Pro Glu Glu Glu Met Leu Cys Glu Val Glu Ile Thr Lys Asn
                325                 330                 335

Tyr Glu Ala Thr Tyr Val Ile Lys Gln Ser Gln Gly Ile Leu Trp Ala
                340                 345                 350

Gly Lys Lys Ile Met Lys Ala Asn Lys Gly Trp Ser Thr Val Lys Asn
        355                 360                 365

Leu Met Leu Leu Leu Gln His Val Ala Thr Glu Ser Ile Thr Arg Val
        370                 375                 380

Gly Lys Cys Pro Thr Phe Lys Val Pro Phe Thr Lys Glu Gln Val Met
385                 390                 395                 400

Trp Glu Met Gln Lys Gly Trp Tyr Tyr Ser Trp Leu Pro Glu Ile Val
                405                 410                 415

Tyr Thr His Gln Val Val His Asp Asp Trp Arg Met Lys Leu Val Glu
                420                 425                 430

Glu Pro Thr Ser Gly Ile Thr Ile Tyr Thr Gly Gly Gly Lys Gln Asn
        435                 440                 445

Gly Glu Gly Ile Ala Ala Tyr Val Thr Ser Asn Gly Arg Thr Lys Gln
        450                 455                 460

Lys Arg Leu Gly Pro Phe Thr His Gln Val Ala Glu Arg Met Ala Ile
465                 470                 475                 480

Gln Met Ala Leu Glu Asp Thr Arg Asp Lys Arg Val Asn Ile Val Thr
                485                 490                 495

Asp Ser Tyr Tyr Cys Trp Lys Asn Ile Thr Glu Gly Leu Gly Leu Glu
                500                 505                 510

Gly Pro Gln Ser Pro Trp Trp Pro Ile Ile Gln Asn Ile His Glu Lys
        515                 520                 525

Glu Ile Val Tyr Phe Ala Trp Val Pro Gly His Lys Gly Ile Cys Gly
        530                 535                 540

Asn Gln Leu Ala Asp Glu Ala Ala Arg Ile Lys Glu Glu Ile
545                 550                 555
```